United States Patent
Luu et al.

(10) Patent No.: US 7,307,098 B2
(45) Date of Patent: Dec. 11, 2007

(54) INDOLE DERIVATIVES AND DRUGS CONTAINING THE SAME

(75) Inventors: Bang Luu, Strasbourg (FR); Djalil Coowar, Strasbourg (FR); Ellane Mohier, Strasbourg (FR); Masashi Yamada, Tokyo (JP); Yukie Suma, Tokyo (JP); Hiroto Suzuki, Tokyo (JP)

(73) Assignee: Meiji Dairies Corporation, Tokyo (JP)

( * ) Notice: Subject to any disclaimer, the term of this patent is extended or adjusted under 35 U.S.C. 154(b) by 346 days.

(21) Appl. No.: 10/520,136

(22) PCT Filed: Jul. 22, 2003

(86) PCT No.: PCT/JP03/09244

§ 371 (c)(1),
(2), (4) Date: Jan. 3, 2005

(87) PCT Pub. No.: WO2004/009545

PCT Pub. Date: Jan. 29, 2004

(65) Prior Publication Data

US 2005/0261357 A1    Nov. 24, 2005

(30) Foreign Application Priority Data

Jul. 19, 2002    (JP)    ................ 2002-211327

(51) Int. Cl.
*A61K 31/404* (2006.01)
*C07D 209/12* (2006.01)

(52) U.S. Cl. .................... 514/415; 548/509
(58) Field of Classification Search ........... 548/509; 514/415
See application file for complete search history.

(56) References Cited

U.S. PATENT DOCUMENTS

| 3,974,179 A | 8/1976 | Demerson et al. |
| 3,996,241 A | 12/1976 | Heerdt et al. |
| 4,053,624 A | 10/1977 | Hubner et al. |
| 4,147,786 A | 4/1979 | Huebner |
| 2002/0058648 A1 | 5/2002 | Hammerly |

FOREIGN PATENT DOCUMENTS

| EP | 747379 | 12/1996 |
| JP | 49-34986 | 9/1974 |
| JP | 6-166672 | 6/1994 |
| JP | 2002-114763 | 4/2002 |
| WO | 98/50357 | 11/1998 |
| WO | 99/08987 | 2/1999 |

OTHER PUBLICATIONS

Hoshino et al, CA 30:45168, 1936.*
Alzheimer's Disease Information page, retrieved from Internet on Apr. 17, 2007, <http://www.ninds.nih.gov/disorders/alzheimersdisease/alzheimersdisease.htm>.*
Selkoe, Apr. 2001, Physiological Reviews, vol. 81(2), pp. 741-766.*
Peripheral neuropathy: Treatment, retrieved from Internet on Apr. 17, 2007, <http://www.mayoclinic.com/print/peripheral-neuropathy/DS00131/DSECTION=8&METHOD=print)>.*
Nelson et al, Current Pharmaceutical Design, 2006, 12, p. 2189 and 2192.*
Stem Cell Information, retrieved from Internet on Apr. 17, 2007, <http://stemcells.nih.gov/info/basics/basics6.asp>.*
Stem Cell Information, retrieved from Internet on Apr. 17, 2007, <http://stemcells.nih.gov/info/scireport/chapter4.asp>.*
Parmar, Paresh: "The Effect of Copper on (3H)- Tryptophan Metabolism in Organ Cultures of Rat Pineal Glands" Metabolic Brain Disease, vol. 16, No. 3/4, Dec. 2001.
Chemical Abstracts, vol. 64, abs.No. 17523c-e, pp. 17523-17524, 1966.
Chemical Abstracts, vol. 53, abs.No. 18972i-18973f, pp. 18971-18974.
Spadoni, Gilberto: "1-[-N-Acylamino(C1-C3)alkyl]indoles as MT1 Melatonin Receptor Partial Agonists, Antagonists, and Putative Inverse Agonists" J.Med.Chem., vol. 41, No. 9, pp. 3624-3634, 1998.

(Continued)

*Primary Examiner*—Kamal A. Saeed
*Assistant Examiner*—Karen Cheng
(74) *Attorney, Agent, or Firm*—Oblon, Spivak, McClelland, Maier & Neustadt, P.C.

(57) ABSTRACT

An indole derivative represented by the following general formula (1):

(1)

[Chemical structure: indole ring with substituents $R^1$, $R^2$, $R^3$, $R^4$ on benzene ring, X at position 3, Y at position 2, NH]

wherein at least one of $R^1$, $R^2$, $R^3$, and $R^4$ represents an alkoxy group containing 1 to 20 carbon atoms, and other groups of the $R^1$, $R^2$, $R^3$, and $R^4$ represent hydrogen, an alkyl group containing 1 to 6 carbon atoms, acetyl group, or hydroxyl group; and either one of X and Y represents —$(CH_2)_n$OH wherein n is an integer of 0 to 30, and the other one of the X and Y represents hydrogen atom; or a salt thereof; and a drug and an agent for promoting differentiation of a stem cell containing such indole derivative or its salt as an effective component, wherein the indole derivative (1) has action of inducing differentiation of neural stem cell specifically into a neuron, and this indole derivative is useful as a prophylactic or therapeutic drug for brain dysfunction or neuropathy caused by loss or degeneration of the neuron.

15 Claims, No Drawings

OTHER PUBLICATIONS

G.A. Bhat: "Synthesis of Indole-2-carbaldehydes, 2-(2-Aminoethyl)- and 2-(2-Amino-propyl)- indoles" J.Chem.Soc. Sec. C: Organic, No. 1, pp. 178-181, 1971.

Tadashi Hirata: "Synthetic Studies on Mitomycins Synthesis of Aziridino_Pyrrolo (1,2-a)Indoles." Tetrahedron Letters, No. 1, pp. 19 to 22, 1969.

Shoji Kamiya: "A Novel Series of Thromboxane A2 Synthetase Inhibitors with Free Radical Scavenging and Anti-peroxidative Activities." Chem.Pharm.Bull., vol. 49, No. 5, pp. 563-571, May 2001.

A.B. Hanley: "Ring Oxygenated Indole Glucosinolates of Brassica Species" Phytochemistry, vol. 24, No. 3, pp. 598-600, 1985.

Chemical Abstracts, 22—Physical Org. Chem., vol. 97, abs.No. 215214, p. 769, 1982.

Chemical Abstracts, 22—Physical Org.Chem., vol. 94, abs.No. 173764, p. 617, 1981.

Chemical Abstracts, vol. 79, abs.No. 41545, p. 284, 1973.

Chemical Abstracts, 27—Heterocycles, vol. 78, abs.No. 43192, 1973.

Chemical Abstracts, AN 1935-60797, XP-002421046.

Hurbert W. Murphy, et al., "Syntheses of Compounds Related to Lysergic Acid", Journal of the American Pharmaceutical Association, Scientific Edition, vol. 32, XP-002421044, 1943, pp. 83-89.

* cited by examiner

INDOLE DERIVATIVES AND DRUGS CONTAINING THE SAME

TECHNICAL FIELD

This invention relates to an indole derivative which has excellent action of inducing neuron differentiation, and which is useful as a prophylactic or therapeutic drug for brain dysfunction, neuropathy, or the like caused by loss or injury of whole neuron including the brain cell. This invention also relates to a drug containing such indole derivative as its effective component.

BACKGROUND ART

Dementia of the Alzheimer type and Parkinson's disease are brain dysfunctions caused by degeneration or loss of neurons. Dementia of the Alzheimer type have been treated by using anticholinesterases or muscarinic receptor agonist. Parkinson's disease has been treated by administration of dopamine or dopamine agonist. Although the symptoms are temporarily improved by the treatments using such drugs, progress of the pathological conditions could be neither stopped nor retarded.

Motor paralysis is a disease wherein voluntary movement is inhibited by the dysfunction of motor nerve extending from the motor center to the muscle. The motor paralysis caused by the dysfunction of the upper motor nerve extending from the cerebrum to the anterior horn cell is called central paralysis, and the motor paralysis caused by the dysfunction of the lower motor nerve extending from the anterior horn cell to muscle is called peripheral paralysis. Motor paralysis is divided into monoplegia (paralysis of a single limb), hemiplegia (paralysis of upper and lower limbs on one side of the body), paraplegia (paralysis of both lower limbs), and quadriplegia depending on the paralyzed part. Although various treatments (such as rehabilitation and neural transplantation) corresponding to individual symptoms have been conducted, there is so far no therapeutic drug that is capable of regenerating the damaged neuron.

Use of a neurotrophic factor such as nerve growth factor (NGF) or brain-derived neurotrophic factor (BDNF) for the prevention or treatment of such diseases may be contemplated. These factors, however, are peptides with high molecular weight, and they are easily decomposed in the living body, and also, they are unable to pass the blood-brain barrier. Accordingly, these factors are strictly limited in their administration route.

In view of the situation as described above, an object of the present invention is to provide a compound which has a sufficiently low molecular weight so that the compound can pass the blood-brain barrier, and which is capable of repairing and regenerating the degenerated or lost neurons to thereby improve various neuropathies.

DISCLOSURE OF THE INVENTION

In view of the situation as described above, the inventors of the present invention conducted an extensive investigation in search of a low molecular weight compound capable of inducing differentiation of neural stem cell into the neuron, and found the indole derivative represented by the general formula (1) as shown below. The present invention has been completed on the bases of such finding.

The present invention provides an indole derivative represented by the following general formula (1):

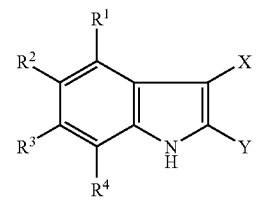

wherein at least one of $R^1$, $R^2$, $R^3$, and $R^4$ represents an alkoxy group containing 1 to 20 carbon atoms, and other groups of the $R^1$, $R^2$, $R^3$, and $R^4$ represent hydrogen, an alkyl group containing 1 to 6 carbon atoms, acetyl group, or hydroxyl group; and either one of X and Y represents —$(CH_2)_n$OH wherein n is an integer of 0 to 30, and the other one of the X and Y represents hydrogen atom; or a salt thereof; and a drug and an agent for promoting differentiation of a stem cell containing such indole derivative or its salt as an effective component.

This invention also provides a pharmaceutical composition containing the indole derivative represented by the above general formula (1) or a its salt, and a pharmaceutically acceptable carrier.

This invention also provides a method for treating brain dysfunction or neuropathy wherein the indole derivative represented by the above general formula (1) or its salt is administered.

This invention also provides use of the indole derivative represented by the above general formula (1) or its salt for producing a drug.

BEST MODE FOR CARRYING OUT THE INVENTION

The indole derivative of the present invention is the one represented by the general formula (1). The alkoxy group represented by $R^1$, $R^2$, $R^3$, or $R^4$ is an alkoxy group containing 1 to 20 carbon atoms, and preferably 1 to 15 carbon atoms. Examples of such alkoxy group include methoxy group, ethoxy group, and propoxy group, with more preferred being methoxy group. Examples of the alkyl group containing 1 to 6 carbon atoms include methyl group, ethyl group, n-propyl group, isopropyl group, and butyl group.

With regard to X or Y, n is a number of 0 to 30, more preferably 1 to 20.

The indole derivative (1) of the present invention is preferably the one wherein at least one of $R^1$, $R^2$, $R^3$, and $R^4$ is an alkoxy group containing 1 to 10 carbon atom, and the remainder of the $R^1$, $R^2$, $R^3$, and $R^4$ is hydrogen atom, and n in X or Y is 10 to 20.

Of the indole derivatives (1) of the present invention, the one wherein X is —$(CH_2)_n$OH, and Y is hydrogen atom may be produced by the reaction scheme as shown below.

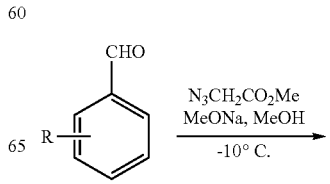

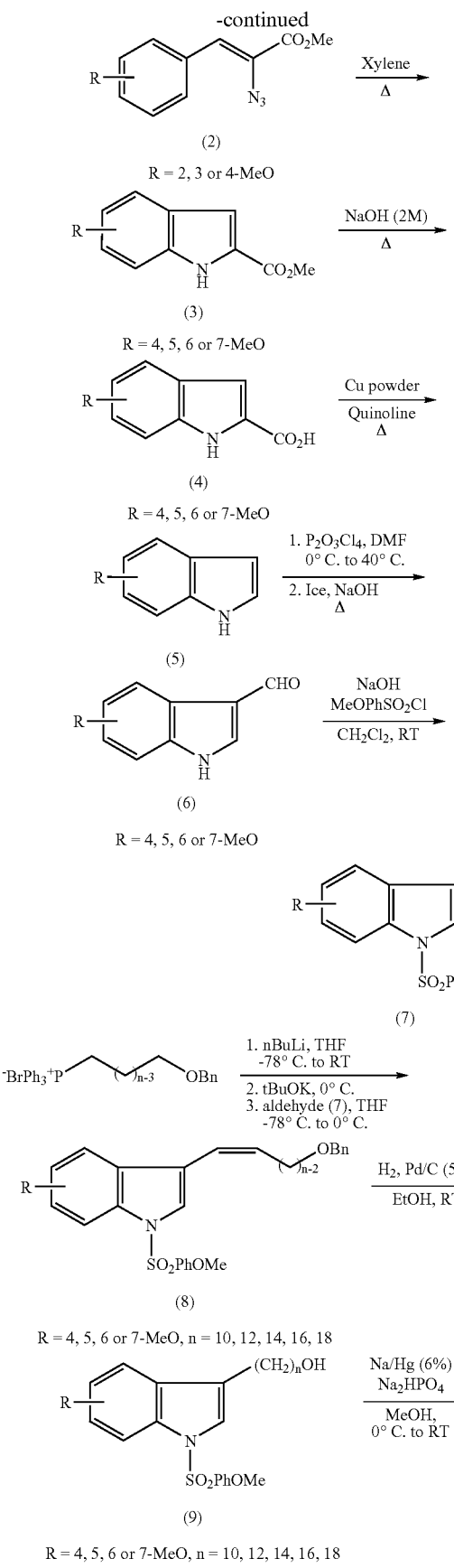

More specifically, an alkoxybenzaldehyde is reacted with methyl azide acetate to produce azide ester (2). This azide ester (2) is dissolved in xylene, and refluxed to produce indole carboxylic acid ester (3). This indole carboxylic acid ester (3) is added to aqueous solution of sodium hydroxide, and the solution was refluxed to produce indole carboxylic acid (4), and this indole carboxylic acid (4) is refluxed in the presence of copper powder and quinoline to produce alkoxy indole (5). To this alkoxy indole (5) is added N,N-dimethylformamide and sodium pyrophosphate, and the solution is refluxed to produce aldehyde (6). This aldehyde (6) is reacted with alkoxybenzene sulfonylchloride to produce aldehyde (7), and this aldehyde (7) is reacted with benzyloxy alkyltriphenyl phosphonium bromide to produce alkene (8). The alkane (8) is hydrogenated to produce compound (9), and this compound (9) is desulfonated to produce indole derivative (1-1).

Of the indole derivative (1) of the present invention, the one wherein X is hydrogen atom and Y is —(CH$_2$)$_n$OH may be produced by the following reaction scheme.

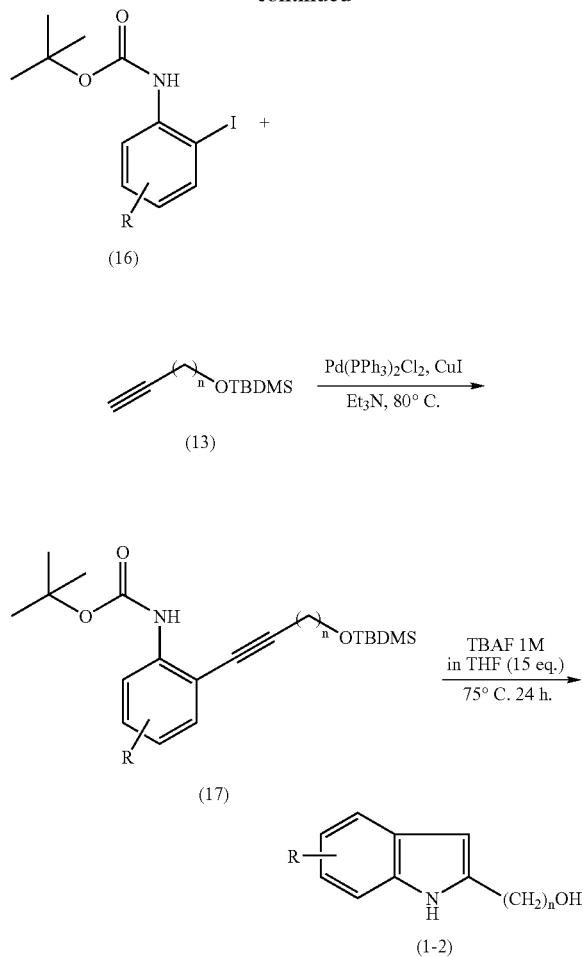

More specifically, hydroxyl group of a bromo-ω-alkanol (11) is protected with silyl group (TBDMSCl), and the bromo-group is substituted by using lithium acetylide to produce alkyne (13). In the meanwhile, aniline (14) is protected with tert-butyl carbamic acid, and iodized to produce iodized aromatic carbarmate ester (16). Next, the resulting iodized aromatic carbarmate ester (16) and the alkyne (13) are allowed to undergo Sonogashira coupling by using $Pd(PPh_3)_4$, CuI, and $Et_3N$ to produce aromatic carbamic acid derivative (17). The protective group on the hydroxyl group is then removed and the amino group moiety is cyclized to produce indole derivative (1-2). In this reaction, 15 equivalents of tetrabutylammonium fluoride is required, and the reaction time (24 to 48 hours) may vary depending on the reactivity of the aniline employed.

The intermediates produced in various steps of the reaction as described above and the resulting indole derivative (1) may be isolated and purified by a method commonly used for the purification in the synthetic organic chemistry, for example, filtration, extraction, washing, drying, concentration, recrystallization, and various chromatographic processes. The intermediates, however, may be used in the subsequent step with no further purification.

The indole derivative (1) of the present invention may be in the form of a pharmaceutically acceptable salt, a solvate or a hydrate thereof. The compound may also be one of various isomers of the compound, and all of such isomers are within the scope of the present invention.

The salt of the indole derivative (1) may be an alkaline metal salt such as sodium, potassium, or lithium salt or an alkaline earth metal salt such as magnesium or calcium salt.

The thus produced indole derivative (1) or its salt of the present invention has action of inducing differentiation of neural stem cell specifically into neuron, and therefore, this indole derivative is useful as a drug such as a prophylactic or therapeutic drug for brain dysfunction (such as dementia of the Alzheimer type or Parkinson's disease) and neuropathy (such as motor paralysis) caused by neuron loss or degeneration or as a promoter for stem cell differentiation.

The drug of the present invention contains the indole derivative (1) or its salt as its effective component, and this derivative (1) and its salt has a low molecular weight. Therefore, the drug can be administered by either by oral administration or perenteral administration (such as intramuscular, subcutaneous, venous or suppository administration).

In producing an oral preparation, the drug of the present invention may be combined with an excipient, and if desired, further with a binder, a disintegrant, a lubricant, a colorant, a corrective, or the like, and produced into a tablet, a coated tablet, granules, a capsule, a solution, a syrup, an elixir, an oil-base or water-base suspension, or the like by a method commonly used in the art.

Exemplary excipients include lactose, corn starch, white sugar, glucose, sorbite, and crystalline cellulose, and exemplary binders include polyvinyl alcohol, polyvinyl ether, ethylcellulose methylcellulose, gumarabic, tragacanth, gelatin, shellac, hydroxypropyl cellulose, hydroxypropyl starch, and polyvinyl pyrrolidone.

Exemplary disintegrants include starch, agar, gelatin powder, crystalline cellulose, calcium carbonate, sodium hydrogencarbonate, calcium citrate, dextran, and pectin, and exemplary lubricants include magnesium stearate, talc, polyethylene glycol, silica, and hardened vegetable oil. Exemplary colorants are those approved for use in the drugs, and exemplary correctives include cocoa powder, peppermint camphor, aromatic acid, peppermint oil, borneol, and cinnamon powder. The tablets and the granules may be provided with an optional coating such as sugar coating and gelatin coating.

In producing a parenteral preparation, the drug of the present invention may be combined with a pH adjusting agent, a buffer, a preservative, or other additives as desired, and produced into the desired preparation by a method commonly used in the art. The solution prepared may be placed in a vessel and produced into a solid preparation, for example, by freeze-drying, and in this case, the solid preparation may be prepared into the desired dosage form immediately before its use. In this case, the solution placed in the vessel may be either the solution of the amount corresponding to a single dose or multiple doses.

The drug of the present invention may be administered at different amount depending on the patient's body weight, age, sex, symptoms, and the like. Typical dose in the case of an adult is 0.001 to 3000 mg, and in particular, 0.01 to 1000 mg per day of the compound represented by the general formula (1), and this dose may be administered as a single dose or in several doses.

EXAMPLES

Next, the present invention is described in further detail by referring to the Examples which by no means limit the scope of the present invention.

Example 1

(1-1) Production of methyl 2-azide-3-(2-methoxyphenyl)-acrylate (2a)

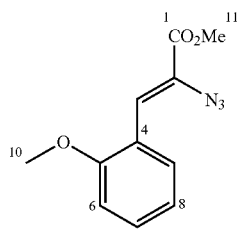

(2a)

A solution of sodium methoxide (30% w/w, 22 mL, 0.12 mol, 4 eq) in methanol (40 mL) was cooled to −10° C. A mixture of 2-methoxybenzaldehyde (4 g, 29.38 mmol, 1 eq) and methyl azide acetate (13.5 g, 0.12 mmol, 4 eq) with methanol (10 mL) was added dropwise to this solution for 1.5 hours. The mixture was stirred for another 1.5 hours at −10° C., poured into ice water (100 mL), and extracted three times with ethyl ether (100 mL). The extracts were combined, washed with aqueous solution of sodium chloride, dried over magnesium sulfate, and concentrated. The concentrate was subjected to silica gel flush chromatography using hexane-ethyl acetate (90-10) to give yellow solid of the title compound (2a) (4.66 g, yield 68%).

TLC: (hexane-AcOEt: 8-2) Rf=0.51 $^1$H NMR (300 MHz), δ: 3.87 (s, 3H, H-11), 3.91 (s, 3H, H-10), 6.89 (d, J=7.9 Hz, 1H, H-6), 6.99 (t, J=7.7 Hz, 1H, H-8), 7.32(dt, J=7.9 Hz, J=1.5 Hz, 1H, H-7), 7.40(s, 1H, H-3), 8.19(dd, J=7.7 Hz, J=1.5 Hz, 1H, H-9). $^{13}$C NMR (75 MHz), δ: 52.81(C-10), 55.57(C-11), 110.44(C-6), 119.64, 120.35(C-3, 8), 122.02 (C-4), 125.05(C-2), 130.56, 130.85(C-7, 9), 157.56(C-5), 164.23(C-1).

(1-2) methyl 2-azide-3-(3-methoxyphenyl)-acrylate (2b)

The title compound (2b) was obtained by a procedure similar to (1-1) (yield 45%).

TLC: (hexane-AcOEt: 8-2) Rf=0.53 $^1$H NMR (300 MHz), δ: 3.84(s, 3H, H-11), 3.91(s, 3H, H-10), 6.89(s, 1H, H-3), 6.92(m, 1H, H-7), 7.30(s, 1H, H-5), 7.33(m, 1H, H-9), 7.43(m, 1H, H-8). $^{13}$C NMR (75 MHz), δ: 52.91(C-10), 55.29(C-11), 115.34, 115.48(C-5, 7), 123.40(C-9), 125.43 (C-3), 125.53(C-2), 129.39(C-8), 134.34(C-4), 159.44(C-6), 163.96(C-1).

(1-3) Production of methyl 2-azide-3-(4-methoxyphenyl)-acrylate (2c)

The title compound (2c) was obtained by a procedure similar to (1-1) (yield 72%).

TLC: (hexane-AcOEt: 8-2) Rf=0.51 $^1$H NMR (300 MHz), δ: 3.84(s, 3H, H-11), 3.89(s, 3H, H-10), 6.89(s, 1H, H-3), 6.91(d, J=9.1 Hz, 1H, H-5,9), 7.79(d, J=9.1 Hz, 1H, H-6,8). $^{13}$C NMR (75 MHz), δ: 52.73(C-10), 55.31(C-11), 113.92 (C-6, 8), 123.07(C-4), 125.69(C-3), 125.96(C-2), 132.39(C-5, 9), 160.50(C-5), 164.25(C-1).

(2-1) Production of methyl 4-methoxy-1H-indole-2-carboxylate (3a)

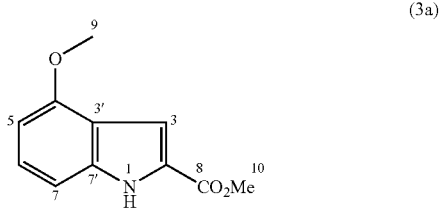

(3a)

The azide ester (2a) (3.7 g, 15.86 mmol, 1 eq) obtained in (1-1) was dissolved in 250 mL of xylene in argon atmosphere. The solution was refluxed for 1 hour, and the solvent was evaporated under reduced pressure. The resulting solid was subjected to silica gel flush chromatography using hexane-ethyl acetate (80-20) to give white solid of the title compound (3a) (2.85 g, yield 88%).

TLC: (hexane-AcOEt: 8-2) Rf=0.26 $^1$H NMR (300 MHz), δ: 3.95(s, 3H, H-9), 3.96(s, 3H, H-10), 6.51(d, J=8.1 Hz, 1H, H-5), 7.03(d, J=8.1 Hz, 1H, H-7), 7.24(t, J=8.1 Hz, 1H, H-6), 7.36(s, 1H, H-3), 9.17(s, 1H, H-1). $^3$C NMR (75 MHz), δ: 51.95(C-9), 55.32(C-10), 99.74(C-5), 104.84(C-7), 106.51(C-3), 118.96(C-3'), 125.78(C-2), 126.45(C-6), 138.31(C-7'), 154.61(C-4), 162.51(C-8).

(2-2) Production of methyl 5-methoxy-1H-indole-2-carboxylate (3b)

The title compound (3b) was obtained by a procedure similar to (2-1) (yield 34%).

TLC: (hexane-CH$_2$Cl$_2$: 5-5) Rf=0.11 $^1$H NMR (300 MHz), δ: 3.85(s, 3H, H-10), 3.94(s, 3H, H-9), 7.00(dd, J=8.9 Hz, J=2.2 Hz, 1H, H-6), 7.08(d, J=2.2 Hz, 1H, H-4), 7.14(s, 1H, H-3), 7.32(d, J=8.9 Hz, 1H, H-7), 8.91(s, 1H, H-1). $^{13}$C NMR (75 MHz), δ: 51.94(C-9), 55.66(C-10), 102.52(C-4), 108.32(C-3), 112.75(C-6), 117.09(C-7), 127.47(C-2), 127.81(C-3'), 132.21(C-7'), 154.72(C-5), 162.35(C-8).

(2-3) Production of methyl 6-methoxy-1H-indole-2-carboxylate (3c)

The title compound (3c) was obtained by a procedure similar to (2-1) (yield 94%).

TLC: (hexane-AcOEt: 8-2) Rf=0.19 $^1$H NMR (300 MHz), δ: 3.85(s, 3H, H-9), 3.94(s, 3H, H-10), 6.83(dd, J=9.5 Hz, J=2.2 Hz, 1H, H-5), 6.84(s, 1H, H-3), 7.17(d, J=2.2 Hz, 1H, H-7), 7.55(d, J=9.5 Hz, 1H, H-4), 9.02(s, 1H, H-1). $^{13}$C NMR (75 MHz), δ: 51.83(C-9), 55.45(C-10), 93.71(C-7), 109.18(C-3), 112.34(C-5), 121.81(C-3'), 123.38(C-4), 125.99(C-2), 138.03(C-7'), 158.90(C-6), 162.50(C-8).

(2-4) Production of methyl 7-methoxy-1H-indole-2-carboxylate (3d)

The title compound (3d) was obtained by a procedure similar to (2-1) (yield 27%).

TLC: (hexane-CH$_2$Cl$_2$: 5-5) Rf=0.30 $^1$H NMR (300 MHz), δ: 3.95(s, 3H, H-9), 3.98(s, 3H, H-10), 6.74(d, J=7.9 Hz, 1H, H-6), 7.08(t, J=7.9 Hz, 1H, H-5), 7.21(s, 1H, H-3), 7.29(d, J=7.9 Hz, 1H, H-4), 9.09(s, 1H, H-1). $^{13}$C NMR (75 MHz), δ: 52.05(C-9), 55.50(C-10), 104.24(C-6), 109.05(C-3), 114.89(C-5), 121.31(C-4), 126.93(C-7'), 128.23(C-3'), 128.71(C-2), 146.58(C-7), 162.32(C-8).

(3-1) Production of 4-methoxy-1H-indole-2-carboxylic acid (4a)

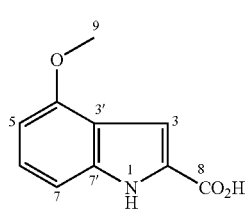
(4a)

The carboxylate (3a) (4 g, 19.49 mmol, 1 eq) obtained in (2-1) was added to aqueous solution of sodium hydroxide (2M, 98 mL, 0.20 mmol, 10 eq). The suspension was stirred and heated until the reaction mixture was uniform, and then refluxed for 30 minutes with heating. The mixture solution was acidified, and the resulting precipitate was extracted three times with ethyl acetate (100 mL). The extracts were combined, washed with water, dried over magnesium sulfate, and concentrated to give white solid of the title compound (4a) (3.71 g, yield 99%).

$^1$H NMR (300 MHz), δ: 3.91(s, 3H, H-9), 6.55 (d, J=7.9 Hz, 1H, H-5) 7.06(d, J=7.9 Hz, 1H, H-7), 7.09(s, 1H, H-3), 7.19(t, J=7.9 Hz, 1H, H-6), 11.79(s, 1H, H-1), 12.87(s, 1H, H-8). $^{13}$C NMR (75 MHz), δ: 55.40(C-9), 99.67(C-5), 104.87, 105.83(C-3, 7), 118.38(C-3'), 125.76(C-6), 127.42 (C-2), 138.92(C-7'), 154.09(C-4), 162.97(C-8).

(3-2) Production of 5-methoxy-1H-indole-2-carboxylic acid (4b)

The title compound (4b) was obtained by a procedure similar to (3-1) (yield 99%).

$^1$H NMR (300 MHz), δ: 3.79(s, 3H, H-9), 6.93(dd, J=8.9 Hz, J=2.2 Hz, 1H, H-6), 7.03(s, 1H, H-3), 7.13(d, J=2.2 Hz, 1H, H-4), 7.36(d, J=8.9 Hz, 1H, H-7), 11.64(s, 1H, H-8), 12.86(s, 1H, H-1). $^{13}$C NMR (75 MHz), δ: 55.12(C-9), 101.89(C-4), 106.84(C-3), 113.26(C-6), 115.70(C-7), 127.06(C-2), 128.52(C-3'), 132.48(C-7'), 153.73(C-4), 162.65(C-8).

(3-3) Production of 6-methoxy-1H-indole-2-carboxylic acid (4c)

The title compound (4c) was obtained by a procedure similar to (3-1) (yield 99%).

$^1$H NMR (300 MHz), δ: 3.81(s, 3H, H-9), 6.75(dd, J=8.8 Hz, J=1.9 Hz, 1H, H-5), 6.90(s, 1H, H-3), 7.05(d, J=1.9 Hz, 1H, H-7), 7.55(d, J=8.8 Hz, 1H, H-4), 11.58(s, 1H, H-1), 12.73(s, 1H, H-8). $^{13}$C NMR (75 MHz), δ: 55.00(C-9), 93.85(C-7), 107.70(C-3), 111.48(C-5), 121.10(C-3'), 122.68 (C-4), 127.09(C-2), 138.22(C-7'), 157.60(C-6), 162.62(C-8).

(3-4) Production of 7-methoxy-1H-indole-2-carboxylic acid (4d)

The title compound (4d) was obtained by a procedure similar to (3-1) (yield 96%).

$^1$H NMR (300 MHz), δ: 3.94(s, 3H, H-9), 6.80 (d, J=7.8 Hz, 1H, H-6) 7.02(d, J=7.8 Hz, 1H, H-5), 7.11(s, 1H, H-3), 7.25(d, J=7.8 Hz, 1H, H-3), 11.65(s, 1H, H-8), 12.82(s, 1H, H-1). $^{13}$C NMR (75 MHz), δ: 56.24(C-9), 105.02(C-6), 109.09(C-3), 115.12(C-5), 121.55(C-4), 129.06, 129.24, 129.53(C-2, 3',7'), 147.65(C-7), 163.46(C-8).

(4-1) Production of 4-methoxy-1H-indole (5a)

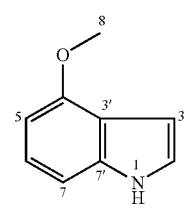
(5a)

The carboxylic acid (4a) (3.65 g, 19.09 mmol, 1 eq), copper powder (849 mg, 13.36 mmol, 0.7 eq) obtained in (3-1) and freshly distilled quinoline (5 mL) were refluxed for 2 hours. The mixture was then cooled, and filtered through a celite filter. The filtrate was poured into ice, and the solution was adjusted to pH 4 with conc. hydrochloric acid, and the solution was extracted three times with ethyl acetate (100 mL). The extracts were combined and washed three times with 2M hydrochloric acid (100 mL), further with saturated sodium hydrogen carbonate, and still further with aqueous solution of sodium chloride. The organic solution was dried over magnesium sulfate, and concentrated. The resulting concentrate was subjected to silica gel flush chromatography using hexane-ethyl acetate (85-15) to give white solid of the title compound (5a) (2.64 g, yield 94%).

TLC: (hexane-AcOEt: 8-2) Rf=0.4 $^1$H NMR (300 MHz), δ: 3.99(s, 3H, H-8), 6.57(d, J=7.9 Hz, 1H, H-5), 6.70(t, J=2.5 Hz, 1H, H-3), 7.03(t, J=7.9 Hz, 1H, H-7), 7.10(t, J=2.5 Hz, 1H, H-2), 7.16(t, J=7.9 Hz, 1H, H-6), 8.13(s, 1H, H-1). $^{13}$C NMR (75 MHz), δ: 53.34(C-8), 99.59, 99.79(C-3, 5), 104.52 (C-7), 118.56(C-3'), 122.73, 122.78(C-2, 6), 137.25(C-7'), 153.39(C-4).

(4-2) Production of 5-methoxy-1H-indole (5b)

The title compound (5b) was obtained by a procedure similar to (4-1) (yield 77%).

TLC: (hexane-AcOEt: 8-2) Rf=0.39 $^1$H NMR (300 MHz), δ: 3.87(s, 3H, H-8), 6.50(t, J=2,8 Hz, 1H, H-3), 6.89(dd, J=8.8 Hz, J=2.4 Hz, 1H, H-6), 7.13(d, J=2.4 Hz, 1H, H-4), 7.19(t, J=2.8 Hz, 1H, H-2), 7.28 (d, J=8.8 Hz, 1H, H-7), 8.06(s, 1H, H-1). $^{13}$C NMR (75 MHz), δ: 55.86(C-8), 102.34, 102.37(C-3, 6), 111.70(C-4), 112.35(C-7), 124.87 (C-2), 130.12(C-3'), 130.97(C-7'), 154.20(C-5).

(4-3) Production of 6-methoxy-1H-indole (5c)

The title compound (5c) was obtained by a procedure similar to (4-1) (yield 87%).

TLC: (hexane-AcOEt: 8-2) Rf=0.38 $^1$H NMR (300 MHz), δ: 3.87(s, 3H, H-8), 6.52(d, J=2.6 Hz, 1H, H-3), 6.85(m, 2H, H-5, 7), 7.08(t, J=2.6 Hz, 1H, H-2), 7.55(d, J=9.1 Hz, 1H, H-4), 7.99(s, 1H, H-1). $^{13}$C NMR (75 MHz), δ: 55.68(C-8), 94.57(C-7), 102.39(C-3), 109.91(C-5), 121.26(C-4), 122.15 (C-3'), 123.09(C-2), 136.55(C-7'), 156.40(C-6).

(4-4) Production of 7-methoxy-1H-indole (5d)

The title compound (5d) was obtained by a procedure similar to (4-1) (yield 66%).

TLC: (hexane-AcOEt: 8-2) Rf=0.45 $^1$H NMR (300 MHz), δ: 3.98(s, 3H, H-8), 6.56(t, J=2.7 Hz, 1H, H-3), 6.67(d, J=7.7 Hz, 1H, H-6), 7.06(t, J=7.7 Hz, 1H, H-5), 7.19(t, J=2.7 Hz, 1H, H-2), 7.29(d, J=7.7 Hz, 1H, H-4), 8.39(s, 1H, H-1). $^{13}$C NMR (75 MHz), δ: 57.63(C-8), 104.04(C-6), 105.21(C-3), 115.76(C-5), 122.47(C-4), 125.98(C-2), 128.79(C-3'), 131.52(C-7'), 148.52(C-7).

(5-1) Production of 4-methoxy-1H-indole-3-carbaldehyde (6a)

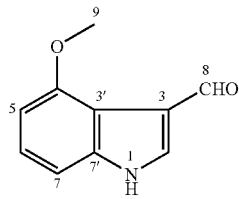

(6a)

A mixture of the indole (5a) (1.7 g, 11.55 mmol, 1 eq) obtained in (4-1) and N,N-dimethylformamide (4.5 mL, 57.76 mmol, 5 eq) was stirred at 0° C., and sodium pyrophosphate (1.9 mL, 13.86 mmol, 1.2 eq) was added dropwise to this mixture. The resulting solution was stirred at 0° C. for 0.5 hour, and then, at 40° C. for 1 hour. Ice, and then, aqueous solution of sodium hydroxide (2M) was added, and the mixture was heated under reflux. The solution was extracted three times with ethyl acetate (50 mL). The extracts were combined, washed with aqueous solution of sodium chloride, dried over magnesium sulfate, and concentrated. The concentrate was subjected to silica gel flush chromatography using hexane-ethyl acetate (60-40) to give white solid of the title compound (6a) (1.72 g, yield 85%).

TLC: (hexane-AcOEt: 6-4) Rf=0.24 $^1$H NMR (300 MHz), δ: 4.00(s, 3H, H-9), 6.72(d, J=8.1 Hz, 1H, H-5), 7.09(d, J=8.1 Hz, 1H, H-7), 7.21(t, J=8.1 Hz, 1H, H-6), 7.92(d, J=3.1 Hz, 1H, H-2), 9.36(s, 1H, H-1), 10.50(s, 1H, H-8). $^{13}$C NMR (75 MHz), δ: 55.24(C-9), 102.18(C-5), 105.74(C-7), 115.49(C-3), 118.03(C-3'), 123.46(C-6), 129.53(C-2), 137.82(C-7'), 153.75(C-4), 186.24(C-8).

(5-2) Production of 5-methoxy-1H-indole-3-carbaldehyde (6b)

The title compound (6b) was obtained by a procedure similar to (5-1) (yield 90%).

TLC: (hexane-AcOEt: 5-5) Rf=0.30 $^1$H NMR (200 MHz), δ: 3.83(s, 3H, H-9), 6.92(dd, J=8.9 Hz, J=2.5 Hz, 1H, H-6), 7.44(d, J=8.9 Hz, 1H, H-7), 7.63(d, J=2.5 Hz, 1H, H-4), 8.25(s, 1H, H-2), 9.93(s, 1H, H-8), 12.06(s, 1H, H-1). $^{13}$C NMR (50 MHz), δ: 55.22 (C-9), 102.46(C-4), 113.10, 113.19(C-6, 7), 117.97(C-3), 124.82(C-3'), 131.73(C-7'), 138.29(C-2), 155.57(C-5), 184.72(C-8).

(5-3) Production of 6-methoxy-1H-indole-3-carbaldehyde (6c)

The title compound (6c) was obtained by a procedure similar to (5-1) (yield 89%).

TLC: (hexane-AcOEt: 6-4) Rf=0.14 $^1$H NMR (300 MHz), δ: 3.82(s, 3H, H-9), 6.85(dd, J=8.6 Hz, J=2.2 Hz, 1H, H-5), 6.99(d, J=2.2 Hz, 1H, H-7), 7.98(d, J=8.6 Hz, 1H, H-4), 8.05(s, 1H, H-2), 9.89(s, 1H, H-8), 12.08(s, 1H, H-1). $^{13}$C NMR (75 MHz), δ: 55.03(C-9), 95.24(C-7), 111.56(C-5), 117.94, 118.24(C-3, 3'), 121.34(C-4), 137.00(C-2), 137.92(C-7'), 156.66(C-6), 184.25(C-8)

(6-1) Production of 4-methoxy-1-(4-methoxybenzsulfonyl)-1H-indole-3-carbaldehyde (7a)

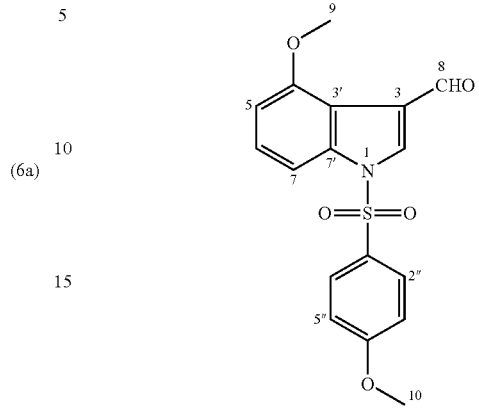

(7a)

To the solution of the compound (6a) (1.68 g, 9.59 mmol, 1 eq) obtained in (5-1) in dichloromethane (20 mL) was added pellets of sodium hydroxide (574 mg, 14.34 mmol, 1.5 eq), and the mixture was stirred at room temperature for 30 minutes. 4-methoxybenzsulfonyl chloride (2.96 g, 14.34 mmol, 1.5 eq) was then added, and the mixture was stirred at room temperature for 12 hours. Ammonium chloride (100 mL) was then added, and the solution was extracted three times with ethyl acetate (100 mL). The extracts were combined, washed with aqueous solution of sodium chloride, dried over magnesium sulfate, and concentrated. The resulting concentrate was subjected to silica gel flush chromatography using hexane-ethyl acetate (70-30) to give white solid of the title compound (7a) (3.15 g, yield 97%).

TLC: (hexane-AcOEt: 6-4) Rf=0.45 $^1$H NMR (300 MHz), δ: 3.84(s, 3H, H-9), 3.95(s, 3H, H-10), 6.99(d, J=8.2 Hz, 1H, H-5), 7.15(d, J=9.0 Hz, 2H, H-3",5"), 7.41(t, J=8.2 Hz, 1H, H-6), 7.61(d, J=8.2 Hz, 1H, H-7), 8.12(d, J=9.0 Hz, 2H, H-2–,6"), 8.40(s, 1H, H-2), 10.40(s, 1H, H-8). $^{13}$C NMR (75 MHz), δ: 55.71, 55,90(C-9, 10), 105.47, 105.97(C-5, 7), 115.21(C-3",5"), 116.43(C-3'), 121.43(C-3), 126.82(C-6), 127.20(C-7'), 129.14(C-2), 129.86(C-2",6"), 135.28(C-1"), 153.88(C-4), 164.32(C-4"), 186.98(C-8).

(6-2) Production of 5-methoxy-1-(4-methoxybenzsulfonyl)-1H-indole-3-carbaldehyde (7b)

The title compound (7b) was obtained by a procedure similar to (6-1) (yield 95%).

TLC: (hexane-AcOEt: 5-5) Rf=0.57 $^1$H NMR (300 MHz), δ: 3.81(s, 3H, H-9), 3.84(s, 3H, H-10), 6.93(d, J=8.9 Hz, 2H, H-3",5"), 6.99(dd, J=9.1 Hz, J=2.5 Hz, 1H, H-6), 7.71(d, J=2.5 Hz, 1H, H-4), 7.81(d, J=9.1 Hz, 1H, H-7), 7.88(d, J=8.9 Hz, 2H, H-2",6"), 8.17(s, 1H, H-2), 10.05(s, 1H, H-8). $^{13}$C NMR (75 MHz), δ: 55.82(C-9, 10), 104.12(C-4), 114.14 (C-6), 114.94(C-3",5"), 116.16(C-7), 122.21(C-3), 127.40 (C-3'), 128.70(C-7'), 129.57(C-2",6"), 135.23(C-1"), 136.69 (C-2), 157.80(C-5), 164.51(C-4"), 185.51(C-8).

(6-3) Production of 6-methoxy-1-(4-methoxybenzsulfonyl)-1H-indole-3-carbaldehyde (7c)

The title compound (7c) was obtained by a procedure similar to (G-1) (yield 97%).

TLC: (hexane-AcOEt: 6-4) Rf=0.39 $^1$H NMR (300 MHz), δ: 3.85(s, 3H, H-9), 3.99(s, 3H, H-10), 7.07(dd, J=8.8 Hz, J=2.2 Hz, 1H, H-5), 7.18(d, J=8.9 Hz, 2H, H-3",5"), 7.44(d, J=2.2 Hz, 1H, H-7), 8.01(d, J=8.8 Hz, 1H, H-4), 8.10(d, J=8.9 Hz, 2H, H-2",6"), 8.77(s, 1H, H-2), 10.05(s, 1H, H-8). $^{13}$C NMR (75 MHz), δ: 55.55, 55.88(C-9, 10), 97.23(C-7), 113.53(C-5), 115.32(C-3",5"), 119.12(C-3'), 121.48(C-3), 122.41(C-4), 127.23(C-7'), 129.69(C-2",6"), 135.42(C-1"), 137.32(C-2), 158.21(C-6), 164.30(C-4"), 186.53(C-8).

(7-1) Production of 3-(10-benzyloxy 1-decenyl)-4-methoxy-1-(4-methoxybenzsulfonyl)-1H-indole
(8a, n=10)

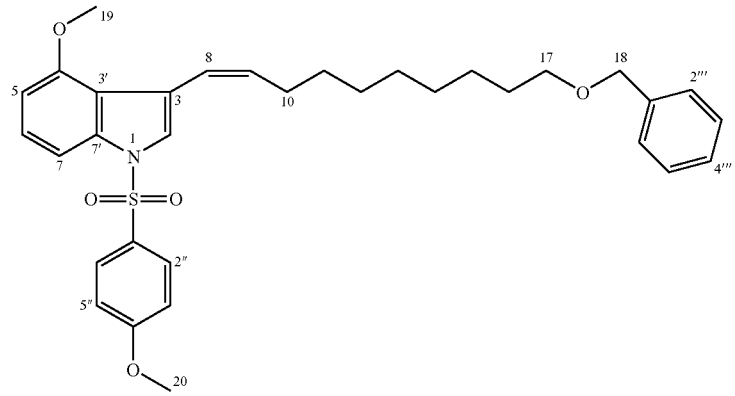

(8a, n = 10)

A solution of nBuLi in hexane (1.5M, 0.7 mL, 1.04 mmol, 1.2 eq) was added dropwise to a solution of 9-benzyloxy-nonyltriphenylphosphonium bromide (600 mg, 1.04 mmol, 1.2 eq) in THF (12 mL) at −78° C. in argon atmosphere. The solution was stirred at room temperature for 15 minutes, and tert-butoxy potassium (117 mg, 1.04 mmol, 1.2 eq) was added at 0° C. The solution was stirred at 0° C. for 15 minutes. The solution was then cooled to −78° C., and to the solution was gradually added a solution of aldehyde (7a) obtained in (6-1) (300 mg, 0.87 mmol, 1 eq) in THF (7 mL). The solution was stirred at −78° C. for 1 hour, and then, at 0° C. for 1.5 hours. The mixed solution was poured into saturated ammonium chloride solution (50 mL), and the solution was extracted three times with ethyl ether (50 mL). The organic phase was combined, washed with aqueous solution of sodium chloride, dried over magnesium sulfate, and concentrated. The resulting concentrate was applied to silica gel using hexane-ethyl acetate (90-10) to (85-15) for the eluate to give white solid of the title compound (8a, n=10) (362 mg, yield 74%).

TLC: (hexane-AcOEt: 8-2) Rf=0.40 $^1$H NMR (300 MHz), δ: 1.33(s br, 8H, H-12 to 15), 1.47(m, 2H, H-16), 1.62(m, 2H, H-11), 2.32(q, J=6.9 Hz, 2H, H-10), 3.47(t, J=6.9 Hz, 2H, H-17), 3.77(s, 3H, H-19), 3.86(s, 3H, H-20), 4.51(s, 2H, H-18), 5.70(dt, J=10.6 Hz, J=6.9 Hz, 1H, H-9), 6.63(d, J=7.8 Hz, 1H, H-5), 6.80(d, J=10.6 Hz, 1H, H-8), 6.86(d, J=8.9 Hz, 2H, H-3",5"), 7.16-7.37(m, 6H, H-7, H-2'" to 6'"), 7.38(s, 1H, H-2), 7.58(t, J=7.8 Hz, 1H, H-6), 7.80(d, J=8.9 Hz, 2H, H-2",6"). $^{13}$C NMR (75 MHz), δ: 26.16(C-10), 29.18-29.76(C-11 to 16), 55.36, 55.58(C-19, 20), 70.49(C-17), 72.84(C-18), 103.87, 104.05(C-3, 5), 106.57(C-7), 114.36(C-3",5"), 119.47(C-3'), 120.53(C-2), 122.46(C-6), 125.58(C-8), 127.43(C-4'"), 127.60(C-2'",6'"), 128.31(C-2",6"), 129.01(C-3'",5'"), 131.69(C-1"), 132.71(C-9), 136.56(C-7'), 138.71(C-1'"), 154.87(C-4), 163.65(C-4").

(7-2) Production of 3-(10-benzyloxy 1-decenyl)-5-methoxy-1-(4-methoxybenzsulfonyl)-1H-indole (8b, n=10)

White solid of the title compound (8b, n=10) was obtained by a procedure similar to (7-1) (yield 65%).

TLC: (hexane-AcOEt: 7-3) Rf=0.49 $^1$H NMR (200 MHz), δ: 1.31 (s br, 8H, H-12 to 15), 1.48 (m, 2H, H-16), 1.61(m, 2H, H-11), 2.30(q, J=6.9 Hz, 2H, H-10), 3.46(t, J=6.4 Hz, 2H, H-17), 3.77(s, 3H, H-19), 3.82(s, 3H, H-20), 4.50(s, 2H, H-18), 5.80(dt, J=11.3 Hz, J=6.9 Hz, 1H, H-9), 6.34(d, J=11.3 Hz, 1H, H-8), 6.85(d, J=8.9 Hz, 2H, H-3",5"), 6.89-6.94(m, 2H, H-4, 6), 7.33(m, 5H, H-2'" to 6'"), 7.45(s, 1H, H-2), 7.78 (d, J=8.9 Hz, 2H, H-2",6"), 7.87(d, J=9.6 Hz, 1H, H-7). $^{13}$C NMR (50 MHz), δ: 26.24(C-10), 29.52-29.82 (C-11 to 16), 55.71(C-19, 20), 70.56(C-17), 72.92(C-18), 102.03(C-4), 113.91(C-6), 114.43(C-3",5"), 114.60(C-3), 117.55(C-7), 119.42(C-3'), 124.33(C-2), 127.51(C-8), 127.68(C-2'",6'"), 128.39(C-3'",5'"), 128.99(C-2",6"), 129.23(C-4'"), 129.60(C-7'), 131.86(C-1"), 134.85(C-9), 138.53(C-1'"), 156.35(C-5), 163.73(C-4").

(7-3) Production of 3-(10-benzyloxy 1-decenyl)-6-methoxy-1-(4-methoxybenzsulfonyl)-1H-indole (8c, n=10)

White solid of the title compound (8c, n=10) was obtained by a procedure similar to (7-1) (yield 91%).

TLC: (hexane-AcOEt: 8-2) Rf=0.32 $^1$H NMR (300 MHz), δ: 1.31(s br, 8H, H-12 to 15), 1.48(m, 2H, H-16), 1.61(m, 2H, H-11), 2.30(q, J=6.7 Hz, 2H, H-10), 3.46(t, J=6.6 Hz, 2H, H-17), 3.78(s, 3H, H-19), 3.88(s, 3H, H-20), 4.50(s, 2H, H-18), 5.79(dt, J=11.5 Hz, J=6.7 Hz, 1H, H-9), 6.35(d, J=11.5 Hz, 1H, H-8), 6.87(d, J=8.9 Hz, 2H, H-3",5"), 6.88(m, 1H, H-5), 7.33(m, 6H, H-4, H-2'" to 6'"), 7.39(s, 1H, H-2), 7.52(d, J=2.0 Hz, 1H, H-7), 7.80(d, J=8.9 Hz, 2H, H-2",6"). $^{13}$C NMR (75 MHz), δ: 26.15(C-10), 29.31-29.75 (C-11 to 16), 55.59, 55.79(C-19, 20), 70.48(C-17), 72.84 (C-18), 97.92(C-7), 112.25(C-5), 114.39(C-3",5"), 117.54 (C-4), 119.23(C-3), 120.02(C-2), 122.16(C-8), 124.73(C-3'), 127.43-128.92 (C-2",6", C-2'" to 6'"), 129.64(C-1"), 134.73(C-9), 135.60(C-7'), 138.71(C-1'"), 158.09(C-5), 163.70(C-4$^{11}$).

(7-4)

The following compounds were produced by procedures similar to (7-1). The yield is shown in Table 1.

3-(12-benzyloxy 1-dodecenyl)-4-methoxy-1-(4-methoxybenzsulfonyl)-1H-indole (8a, n=12), 3-(14-benzyloxy 1-tetradecenyl)-4-methoxy-1-(4-methoxybenzsulfonyl)-1H-indol e (8a, n=14), 3-(16-benzyloxy 1-hexadecenyl)-4-methoxy-1-(4-methoxybenzsulfonyl)-1H-indole (8a, n=16), 3-(18-benzyloxy 1-octadecenyl)-4-methoxy-1-(4-methoxybenzsulfonyl)-1H-indole (8a, n=18), 3-(12-benzyloxy 1-dodecenyl)-5-methoxy-1-(4-methoxybenzsulfonyl)-1H-indole (8b, n=12), 3-(14-benzyloxy 1-tetradecenyl)-5-methoxy-1-(4-methoxybenzsulfonyl)-1H-indol e (8b, n=14), 3-(16-benzyloxy 1-hexadecenyl)-5-methoxy-1-(4-methoxybenzsulfonyl)-1H-indole (8b, n=16), 3-(18-benzyloxy 1-octadecenyl)-5-methoxy-1-(4-methoxybenzsulfonyl)-1H-indole (8b, n=18), 3-(12-benzyloxy 1-dodecenyl)-6-methoxy-1-(4-methoxybenzsulfonyl)-1H-indole (8c, n=12)

TABLE 1

| | | X = —$(CH_2)_n$OH | | |
|---|---|---|---|---|
| R | n | Formula | MW | Yield |
| 8a 4-MeO | 10 | $C_{33}H_{39}NO_5S$ | 561.73 | 74% |
| | 12 | $C_{35}H_{43}NO_5S$ | 589.79 | 71% |
| | 14 | $C_{37}H_{47}NO_5S$ | 617.84 | 45% |
| | 16 | $C_{39}H_{51}NO_5S$ | 645.89 | 69% |
| | 18 | $C_{41}H_{55}NO_5S$ | 673.95 | 68% |
| 8b 5-MeO | 10 | $C_{33}H_{39}NO_5S$ | 561.73 | 65% |
| | 12 | $C_{35}H_{43}NO_5S$ | 589.79 | 62% |
| | 14 | $C_{37}H_{47}NO_5S$ | 617.84 | 84% |
| | 16 | $C_{39}H_{51}NO_5S$ | 645.89 | 94% |
| | 18 | $C_{41}H_{55}NO_5S$ | 673.95 | 71% |
| 8c 6-MeO | 10 | $C_{33}H_{39}NO_5S$ | 561.73 | 91% |
| | 12 | $C_{35}H_{43}NO_5S$ | 589.79 | 78% |

(8-1) Production of 10-[4-methoxy-1-(4-methoxybenzsulfonyl)-1H-indole-3-yl]-deca ne-1-ol
(9a, n=10)

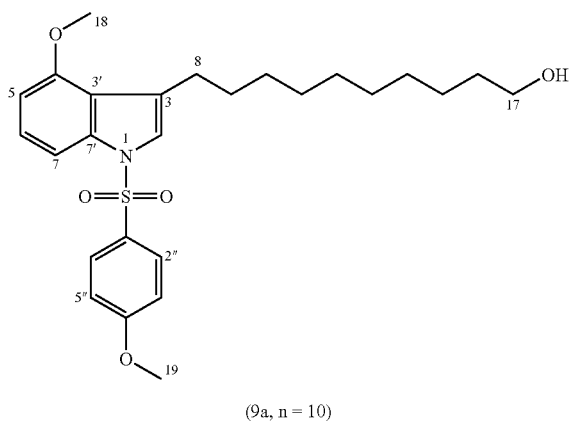

(9a, n = 10)

Pd—C (5%, 35 mg, 10 mol %) was added to solution of the alkene obtained in (7-1) (8a, n=10) (350 mg, 0.62 mmol, 1 eq) in ethanol (6 mL). The mixed solution was stirred at room temperature in hydrogen atmosphere of 1 atm. for 4 hours. The mixture was then filtered through celite, and concentrated. The resulting concentrate was subjected to silica gel flush column chromatography using hexane-ethyl acetate (70-30) to give white solid of the title compound (9a, n=10) (277 mg, yield 93%).

TLC: (hexane-AcOEt: 7-3) Rf=0.13 $^1$H NMR (300 MHz), δ: 1.27(s br, 12H, H-10 to 15), 1.59(m, 4H, H-9,16), 2.76(t, J=7.3 Hz, 2H, H-8), 3.64(t, J=6.2 Hz, 2H, H-17), 3.78(s, 3H, H-18), 3.85(s, 3H, H-19), 6.61(d, J=8.2 Hz, 1H, H-5), 6.85(d, J=8.9 Hz, 2H, H-3",5"), 7.15(s, 1H, H-2), 7.18(t, J=8.2 Hz, 1H, H-6), 7.56(d, J=8.2 Hz, 1H, H-7), 7.77(d, J=8.9 Hz, 2H, H-2",6"). $^{13}$C NMR (75 MHz), δ: 25.72(C-15S), 26.85(C-9), 29.34-29.80(C-8,10 to 14), 32.79(C-16), 55.18, 55.55(C-18, 19), 63.09(C-17), 103.55(C-5), 106.62 (C-7), 114.25(C-3",5"), 120.59(C-3), 121.24(C-6), 124.10 (C-3'), 125.27(C-2), 128.93(C-2",6"), 129.83(C-1"), 136.95 (C-7'), 154.62(C-4), 163.50(C-4").

(8-2) Production of 10-[5-methoxy-1-(4-methoxybenzsulfonyl)-1H-indole-3-yl]-deca ne-1-ol
(9b, n=10)

White solid of the title compound (9b, n=10) was obtained by a procedure similar to (8-1) (yield 84%).

TLC: (hexane-AcOEt: 7-3) Rf=0.21 $^1$H NMR (200 MHz), δ: 1.29(s br, 12H, H-10 to 15), 1.60(m, 4H, H-9,16), 2.58(t, J=7.4 Hz, 2H, H-8), 3.64(t, J=6.4 Hz, 2H, H-17) 3.77(s, 3H, H-18), 3.82(s, 3H, H-19), 6.83(d, J=8.9 Hz, 2H, H-3",5"), 6.88-6.93(m, 2H, H-4,6), 7.24(s, 1H, H-2), 7.86(d, J=9.6 Hz, 1H, H-7), 7.75(d, J=8.9 Hz, 2H, H-2",6") $^{13}$C NMR (50 MHz), δ: 24.92(C-15), 25.79(C-9), 28.71(C-8), 29.42-29.59 (C-10 to 14), 32.85(C-16), 55.63, 55.76(C-18, 19), 63.10 (C-17), 102.31(C-4), 113.20(C-6), 114.31(C-3",5"), 114.74 (C-7), 123.56(C-2), 123.95(C-3), 128.92(C-2",6"), 129.87 (C-7'), 130.19(C-3'), 132.35(C-1"), 156.31(C-5), 163.58 (C-4").

(8-3) Production of 10-[6-methoxy-1-(4-methoxybenzsulfonyl)-1H-indole-3-yl]-deca ne-1-ol
(9c, n=10)

White solid of the title compound (9c, n=10) was obtained by a procedure similar to (8-1) (yield 80%).

TLC: (hexane-AcOEt: 7-3) Rf=0.21 $^1$H NMR (300 MHz), δ: 1.28(s br, 12H, H-10 to 15), 1.58(m, 4H, H-9,16), 2.58(t, J=7.3 Hz, 2H, H-8), 3.63(t, J=6.6 Hz, 2H, H-17) 3.78(s, 3H, H-18), 3.87(s, 3H, H-19), 6.85(d, J=8.9 Hz, 2H, H-3",5"), 6.86(m, 1H, H-5), 7.17(s, 1H, H-2), 7.32(d, J=8.6 Hz, 1H, H-4), 7.52(d, J=2.2 Hz, 1H, H-7), 7.77(d, J=8.9 Hz, 2H, H-2",6"). $^{13}$C NMR (75 MHz), δ: 24.89(C-15), 25.70(C-9), 28.81(C-8), 29.34-29.52(C-10 to 14), 32.77(C-16), 55.56, 55.78(C-18, 19), 63.03(C-17), 98.22(C-7), 111.88(C-5), 114.28(C-3",5"), 119.94(C-4), 121.29(C-2), 123.60(C-3), 125.09(C-3'), 128.85(C-2",6"), 129.84(C-1"), 136.39(C-7'), 157.87(C-6), 163.53(C-4").

(8-4)

The following compounds were produced by procedures similar to (8-1). The yield is shown in Table 2.

12-[4-methoxy-1-(4-methoxybenzsulfonyl)-1H-indole-3-yl]-dodecane-1-ol (9a, n=12), 14-[4-methoxy-1-(4-methoxybenzsulfonyl)-1H-indole-3-yl]-tetradecane-1-ol (9a, n=14), 16-[4-methoxy-1-(4-methoxybenzsulfonyl)-1H-indole-3-yl]-hexadecane-1-ol (9a, n=16), 18-[4-methoxy-1-(4-methoxybenzsulfonyl)-1H-indole-3-yl]-octadecane-1-ol (9a, n=18), 12-[5-methoxy-1-(4-methoxybenzsulfonyl)-1H-indole-3-yl]-dodecane-1-ol (9b, n=12), 14-[5-methoxy-1-(4-methoxybenzsulfonyl)-1H-indole-3-yl]-tetradecane-1-ol (9b, n=14), 16-[5-methoxy-1-(4-methoxybenzsulfonyl)-1H-indole-3-yl]-hexadecane-1-ol (9b, n=16), 18-[5-methoxy-1-(4-methoxybenzsulfonyl)-1H-indole-3-yl]-octadecane-1-ol (9b, n=18), 12-[6-methoxy-1-(4-methoxybenzsulfonyl)-1H-indole-3-yl]-dodecane-1-ol (9c, n=12)

TABLE 2

|  |  | X = —(CH$_2$)$_n$OH |  |  |
|---|---|---|---|---|
|  | R | n | Formula | MW | Yield |
| 9a | 4-MeO | 10 | C$_{26}$H$_{35}$NO$_5$S | 473.63 | 93% |
|  |  | 12 | C$_{28}$H$_{39}$NO$_5$S | 501.68 | 94% |
|  |  | 14 | C$_{30}$H$_{43}$NO$_5$S | 529.73 | 57% |
|  |  | 16 | C$_{32}$H$_{47}$NO$_5$S | 557.79 | 47% |
|  |  | 18 | C$_{34}$H$_{51}$NO$_5$S | 585.84 | 50% |
| 9b | 5-MeO | 10 | C$_{26}$H$_{35}$NO$_5$S | 473.63 | 84% |
|  |  | 12 | C$_{28}$H$_{39}$NO$_5$S | 501.68 | 95% |
|  |  | 14 | C$_{30}$H$_{43}$NO$_5$S | 529.73 | 91% |
|  |  | 16 | C$_{32}$H$_{47}$NO$_5$S | 557.79 | 91% |
|  |  | 18 | C$_{34}$H$_{51}$NO$_5$S | 585.84 | 94% |
| 9c | 6-MeO | 10 | C$_{26}$H$_{35}$NO$_5$S | 473.63 | 80% |
|  |  | 12 | C$_{28}$H$_{39}$NO$_5$S | 501.68 | 85% |

(9-1) Production of 10-(5-methoxy-1H-indole-3-yl)-decane-1-ol (1-1a, n=10)

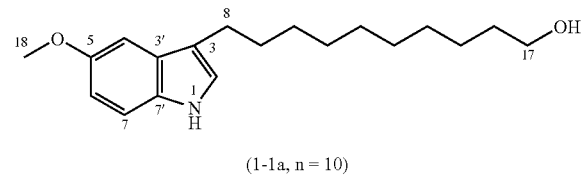

(1-1a, n = 10)

To the solution of the indole (9b, n=10) (288 mg, 0.61 mmol, 1 eq) obtained in (8-2) in dry methanol (10 mL) were added disodium hydrogenphosphate (173 mg, 1.22 mmol, 2 eq) and sodium amalgam (6%, 5 g) at 0° C. argon atmosphere. The mixture was stirred at room temperature for 12 hours, quenched with saturated solution of ammonium chloride (50 mL), and extracted three times with ethyl ether (50 mL). The extracts were combined, washed with aqueous solution of sodium chloride, dried over magnesium sulfate, and concentrated. The resulting concentrate was applied to silica gel using hexane-ethyl acetate (80-20) to (75-25) for the eluate to obtain white crystals of the title compound (1-1a, n=10) (155 mg, yield 84%).

TLC: (hexane-AcOEt: 6-4) Rf=0.38 $^1$H NMR (200 MHz), δ: 1.30(s br, 12H, H-10 to 15), 1.57(m, 2H, H-16), 1.71(m, 2H, H-9), 2.71(t, J=7.4 Hz, 2H, H-8), 3.64(t, J=6.4 Hz, 2H, H-17), 3.88(s, 3H, H-18), 6.85(dd, J=8.9 Hz, J=2.2 Hz, 1H, H-6), 6.94(s, 1H, H-2), 7.05(d, J=2.2 Hz, 1H, H-4), 7.24(d, J=8.9 Hz, 1H, H-7), 7.86(s, 1H, H-1) $^{13}$C NMR (50 MHz), δ: 25.22 (C-15), 25.79(C-9), 29.48-29.64(C-10 to 14), 30.04 (C-8), 32.87(C-16), 56.08(C-18), 63.15(C-17), 101.15(C-4), 111.75, 111.92(C-6, 7), 116.95(C-3), 121.99(C-2), 128.08 (C-3'), 131.65(C-7'), 153.82(C-5).

(9-2) Production of 10-(4-methoxy-1H-indole-3-yl)-decane-1-ol (1-1b, n=10)

White crystal of the title compound (1-1b, n=10) was obtained by the procedure similar to (9-1) (yield 85%).

TLC: (hexane-AcOEt: 6-4) Rf=0.43 $^1$H NMR (300 MHz), δ: 1.31(s br, 12H, H-10 to 15), 1.57(m, 2H, H-16), 1.68(m, 2H, H-9), 2.87(t, J=7.5 Hz, 2H, H-8), 3.64(t, J=6.2 Hz, 2H, H-17), 3.92(s, 3H, H-18), 6.48(d, J=7.8 Hz, 1H, H-5), 6.82(s, 1H, H-2), 6.94(d, J=7.8 Hz, 1H, H-7), 7.07(t, J=7.8 Hz, 1H, H-6), 7.88(s, 1H, H-1). $^{13}$C NMR (75 MHz), δ: 25.73(C-15), 26.87(C-9), 29.43-29.60(C-10 to 14), 31.15(C-8), 32.79(C-16), 55.08(C-18), 63.10(C-17), 99.25(C-7), 104.32(C-5), 117.46(C-3), 117.84(C-3'), 119.68(C-6), 122.52(C-2), 138.10(C-7'), 155.02(C-4).

(9-3). Production of 14-(4-methoxy-1H-indole-3-yl)-tetradecane-1-ol (1-1b, n=14)

White crystal of the title compound (1-1b, n=14) was obtained by the procedure similar to (9-1) (yield 99%).

TLC: (hexane-AcOEt: 7-3) Rf=0.25 $^1$H-NMR (300 MHz), δ: 1.27(s br, 12H, H-10 to 19), 1.57(m, 2H, H-20), 1.68(m, 2H, H-9), 2.86(t, J=7.3 Hz, 2H, H-8), 3.64(t, J=6.4 Hz, 2H, H-21), 3.92(s, 3H, H-22), 6.47(d, J=7.8 Hz, 1H, H-5), 6.82(s, 1H, H-2), 6.94(d, J=7.8 Hz, 1H, H-7), 7.07(t, J=7.8 Hz, 1H, H-6), 7.88(s, 1H, H-1). $^{13}$C NMR (75 MHz), δ: 25.72(C-19), 26.88(C-9), 29.42-29.69(C-10 to 18), 31.18 (C-8), 32.80(C-20), 55.07(C-22), 63.10(C-21), 99.23(C-7), 104.31(C-5), 117.45(C-3), 117.88(C-3'), 119.65(C-6), 122.52(C-2), 138.08(C-7'), 155.02(C-4).

(9-4) Production of 10-(6-methoxy-1H-indole-3-yl)-decane-1-ol (1-1c, n=10)

White crystal of the title compound (1-1c, n=10) was obtained by the procedure similar to (9-1) (yield 84%).

TLC: (hexane-AcOEt: 7-3) Rf=0.14 $^1$H NMR (300 MHz), δ: 1.30(s br, 12H, H-10 to 15), 1.56(m, 2H, H-16), 1.69(m, 2H, H-9), 2.71(t, J=7.3 Hz, 2H, H-8), 3.64(m, 2H, H-17), 3.85(s, 3H, H-18), 6.79(dd, J=8.6 Hz, J=2.2 Hz, 1H, H-5), 6.85(s, 1H, H-2), 6.87(m, 1H, H-7), 7.47(d, J=8.6 Hz, 1H, H-4), 7.81(s, 1H, H-1). $^{13}$C NMR (75 MHz), δ: 25.20(C-15), 25.71(C-9), 29.39-29.57(C-10 to 14), 30.14(C-8), 32.79(C-16), 55.69(C-18), 63.08(C-17), 94.62(C-7), 108.95(C-5), 117.11(C-3), 119.56; 119.71(C-2, 4), 122.12(C-3'), 137.04 (C-7'), 156.37(C-6).

(9-5)

The following indole derivatives (1-1) were produced by procedures similar to (9-1). All of these compounds were obtained in the form of white crystals. The yield is shown in Table 3. The analytical data are shown in Tables 4 to 6.

12-(5-methoxy-1H-indole-3-yl)-dodecane-1-ol (1-1a, n=12), 14-(5-methoxy-1H-indole-3-yl)-tetradecane-1-ol (1-1a, n=14), 16-(5-methoxy-1H-indole-3-yl)-hexadecane-1-ol (1-1a, n=16), 18-(5-methoxy-1H-indole-3-yl)-octadecane-1-ol (1-1a, n=18), 12-(4-methoxy-1H-indole-3-yl)-dodecane-1-ol (1-1b, n=12), 16-(4-methoxy-1H-indole-3-yl)-hexadecane-1-ol (1-1b, n=16), 18-(4-methoxy-1H-indol-3-yl)-octadecane-1-ol (1-1b, n=18), 12-(6-methoxy-1H-indol-3-yl)-dodecane-1-ol (1-1c, n=12)

14-(6-methoxy-1H-indol-3-yl)-tetradecane-1-ol (1-1c, n=14), 16-(6-methoxy-1H-indol-3-yl)-hexadecane-1-ol (1-1c, n=16)

TABLE 3

$X = -(CH_2)_nOH$

| | R | n | Formula | MW | Yield |
|---|---|---|---|---|---|
| 1-1b | 4-MeO | 10 | $C_{19}H_{29}NO_2$ | 303.44 | 85% |
| | | 12 | $C_{21}H_{33}NO_2$ | 331.49 | 82% |
| | | 14 | $C_{23}H_{37}NO_2$ | 359.55 | 99% |
| | | 16 | $C_{25}H_{41}NO_2$ | 387.60 | 92% |
| | | 18 | $C_{27}H_{45}NO_2$ | 415.65 | 96% |
| 1-1a | 5-MeO | 10 | $C_{19}H_{29}NO_2$ | 303.44 | 84% |
| | | 12 | $C_{21}H_{33}NO_2$ | 331.49 | 95% |
| | | 14 | $C_{23}H_{37}NO_2$ | 359.55 | 87% |
| | | 16 | $C_{25}H_{41}NO_2$ | 387.60 | 91% |
| | | 18 | $C_{27}H_{45}NO_2$ | 415.65 | 85% |
| 1-1c | 6-MeO | 10 | $C_{19}H_{29}NO_2$ | 303.44 | 84% |
| | | 12 | $C_{21}H_{33}NO_2$ | 331.49 | 80% |
| | | 14 | $C_{23}H_{37}NO_2$ | 359.55 | 92% |
| | | 16 | $C_{25}H_{41}NO_2$ | 387.60 | 91% |

TABLE 4

| | R | n | Analysis |
|---|---|---|---|
| 1-1b | 4-MeO | 10 | m.p: 66-67° C.<br>UV (acetonitrile): $\lambda_{max}$: 225 nm ($\epsilon$ 301465); 270 nm ($\epsilon$ 71091); 283 nm ($\epsilon$ 67263); 293 nm ($\epsilon$ 68010)<br>MS (EI): 303.4($M^+$, 25); 160.3($C_{10}H_{10}NO$, 100); 130.4($C_9H_8N$, 17)<br>Analysis (%):<br>calculated: C: 75.21, H: 9.63, N: 4.62, O: 10.55<br>found: C: 75.45, H: 9.71, N: 4.54, O: 10.30 |
| | | 12 | m.p: 45-46° C.<br>UV (acetonitrile): $\lambda_{max}$: 226 nm ($\epsilon$ 287495); 270 nm ($\epsilon$ 81272); 283 nm ($\epsilon$ 75913); 292 nm ($\epsilon$ 73019)<br>MS (EI): 331.4($M^+$, 32); 160.3($C_{10}H_{10}NO$, 100); 130.4($C_9H_8N$, 16)<br>Analysis (%):<br>calculated: C: 76.09, H: 10.03, N: 4.23, O: 9.65<br>found: C: 76.02, H: 10.10, N: 4.12, O: 9.76 |
| | | 14 | m.p: 48-49° C.<br>UV (acetonitrile): $\lambda_{max}$: 225 nm ($\epsilon$ 288010); 270 nm ($\epsilon$ 66570); 283 nm ($\epsilon$ 62650); 293 nm ($\epsilon$ 60840)<br>MS (EI): 359.5($M^+$, 35); 160.3($C_{10}H_{10}NO$, 100); 130.4($C_9H_8N$, 16)<br>Analysis (%):<br>calculated: C: 76.83, H: 10.37, N: 3.90, O: 8.90<br>found: C: 77.15, H: 10.52, N: 3.77, O: 8.56 |
| | | 16 | m.p: 53-54° C.<br>UV (acetonitrile): $\lambda_{max}$: 225 nm ($\epsilon$ 295827); 270 nm ($\epsilon$ 68194); 283 nm ($\epsilon$ 64214); 293 nm ($\epsilon$ 62969)<br>MS (EI): 387.5($M^+$, 43); 160.3($C_{10}H_{10}NO$, 100); 130.3($C_9H_8N$, 15)<br>Analysis (%):<br>calculated: C: 77.47, H: 10.66, N: 3.61, O: 8.26<br>found: C: 77.62, H: 10.76, N: 3.54, O: 8.08 |
| | | 18 | m.p: 65-66° C.<br>UV (acetonitrile): $\lambda_{max}$: 225 nm ($\epsilon$ 290535); 270 nm ($\epsilon$ 69000); 283 nm ($\epsilon$ 64861); 293 nm ($\epsilon$ 63535)<br>MS (EI): 415.5($M^+$, 41); 160.3($C_{10}H_{10}NO$, 100); 130.3($C_9H_8N$, 15)<br>Analysis (%):<br>Calculated C: 78.02, H: 10.91, N: 3.37, O: 7.70<br>found: C: 78.01, H: 10.98, N: 3.29, O: 7.72 |

TABLE 5

| | R | n | Analysis |
|---|---|---|---|
| 1-1a | 5-MeO | 10 | m.p: 75-76° C.<br>UV (acetonitrile): $\lambda_{max}$: 206 nm ($\epsilon$ 209091); 225 nm ($\epsilon$ 218030); 278 nm ($\epsilon$ 57697); 297 nm ($\epsilon$ 45465)<br>MS (EI): 303.4 ($M^+$, 25); 160.3 ($C_{10}H_{10}NO$, 100); 145.3 ($C_9H_7NO$, 7)<br>Analysis (%):<br>calculated: C: 75.21, H: 9.63, N: 4.62, O: 10.55<br>found: C: 75.59, H: 9.79, N: 4.51, O: 10.11 |
| | | 12 | m.p: 82-83° C.<br>UV (acetonitrile): $\lambda_{max}$: 206 nm ($\epsilon$ 229893); 226 nm ($\epsilon$ 256951); 278 nm ($\epsilon$ 77806); 298 nm ($\epsilon$ 58825)<br>MS (EI): 331.4 ($M^+$, 28); 160.3 ($C_{10}H_{10}NO$, 100); 145.3 ($C_9H_7NO$, 6)<br>Analysis (%):<br>calculated: C: 76.09, H: 10.03, N: 4.23, O: 9.65<br>found: C: 76.43, H: 10.15, N: 4.11, O: 9.31 |
| | | 14 | m.p: 87-88° C.<br>UV (acetonitrile): $\lambda_{max}$: 207 nm ($\epsilon$ 245040); 225 nm ($\epsilon$ 272280); 278 nm ($\epsilon$ 84870); 297 nm ($\epsilon$ 64200)<br>MS (EI): 359.5 ($M^+$, 35); 160.3 ($C_{10}H_{10}NO$, 100); 145.3 ($C_9H_7NO$, 6)<br>Analysis (%):<br>calculated: C: 76.83, H: 10.37, N: 3.90, O: 8.90<br>found: C: 76.86, H: 10.49, N: 3.81, O: 8.84 |
| | | 16 | m.p: 92-93° C.<br>UV (acetonitrile): $\lambda_{max}$: 207 nm ($\epsilon$ 231449); 225 nm ($\epsilon$ 249020); 278 nm ($\epsilon$ 78327); 297 nm ($\epsilon$ 58439)<br>MS (EI): 387.5 ($M^+$, 35); 160.3 ($C_{10}H_{10}NO$, 100); 145.3 ($C_9H_7NO$, 5)<br>Analysis (%):<br>calculated: C: 77.47, H: 10.66, N: 3.61, O: 8.26<br>found: C: 77.76, H: 10.78, N: 3.57, O: 7.89 |
| | | 18 | m.p: 94-95° C.<br>UV (acetonitrile): $\lambda_{max}$: 207 nm ($\epsilon$ 250653); 225 nm ($\epsilon$ 285366); 278 nm ($\epsilon$ 94624); 297 nm ($\epsilon$ 70594)<br>MS (EI): 415.5 ($M^+$, 38); 160.3 ($C_{10}H_{10}NO$, 100); 145.3 ($C_9H_7NO$, 5)<br>Analysis (%):<br>Calculated C: 78.02, H: 10.91, N: 3.37, O: 7.70<br>Found C: 77.88, H: 10.99, N: 3.29, O: 7.84 |

TABLE 6

| | R | n | Analysis |
|---|---|---|---|
| 1-1c | 6-MeO | 10 | m.p: 88-89° C.<br>UV (acetonitrile): $\lambda_{max}$: 206 nm ($\epsilon$ 189323); 228 nm ($\epsilon$ 279970); 275 nm ($\epsilon$ 56545); 292 nm ($\epsilon$ 57990)<br>MS (EI)+: 303.3 ($M^+$, 31); 160.3 ($C_{10}H_{10}NO$, 100); 145.3 ($C_9H_7NO$, 8)<br>Analysis (%):<br>calculated: C: 75.21, H: 9.63, N: 4.62, O: 10.55<br>found: C: 75.51, H: 9.80, N: 4.48, O: 10.21 |
| | | 12 | m.p: 95-96° C.<br>UV (acetonitrile): $\lambda_{max}$: 204 nm ($\epsilon$ 165544); 229 nm ($\epsilon$ 252631); 276 nm ($\epsilon$ 39748); 294 nm ($\epsilon$ 44272)<br>MS (EI): 331.4 ($M^+$, 32); 160.3 ($C_{10}H_{10}NO$, 100); 145.3 ($C_9H_7NO$, 7)<br>Analysis (%):<br>calculated: C: 76.09, H: 10.03, N: 4.23, O: 9.65<br>found: C: 76.31, H: 10.16, N: 4.17, O: 9.36 |

Example 2

(1) Production of tert-butyl-hexadecane-15-ynyloxy-dimethylsilane (13a)

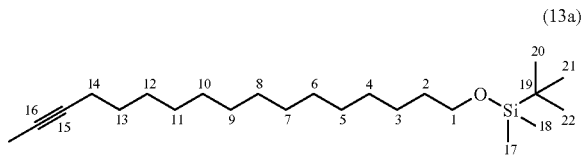

(13a)

The solution of (14-bromo-tetradecyloxy)-tert-butyl-dimethylsilane (8.9 g, 21.4 mmol, 1 eq) in DMSO (10 mL) was added dropwise to the solution of N,N-diethylethane-1,2-diamine lithium acetylide (3.1 g, 33.2 mmol, 1.5 eq) in DMSO (15 mL) at 0° C. This solution was stirred at room temperature for 6 hours, poured into saturated aqueous solution of potassium chloride (100 mL), and extracted three times with hexane (100 mL). The extract was washed with aqueous solution of sodium chloride, dried over magnesium sulfate, and concentrated. The resulting concentrate was subjected to silica gel flush column chromatography (eluate: hexane-$CH_2Cl_2$=80-20) to obtain the colorless liquid of the title compound (6.12 g, yield 81%).

MW: ($C_{22}H_{44}OSi$) 352.67. TLC: (hexane-$CH_2Cl_2$: 9-1) Rf=0.38. $^1$H NMR (300 MHz, $CDCl_3$), δ: 0.04(s, 6H, H-17,18), 0.90(s, 9H, H-20,21,22), 1.25-1.55(m, 24H, H-3 to 13), 1.93(t, J=2.5 Hz, 1H, H-16), 2.15(td, J=7.0 Hz, J=2.7 Hz, 2H, H-14), 3.59(t, J=6.6 Hz, 2H, H-1). $^{13}$C NMR (75 MHz, $CDCl_3$), δ: −5.28(C-17, 18), 18.38(C-14), 18.41(C-19), 25.96(C-20, 21, 22), 28.48-29.61(C-3 to 13), 32.86(C-2), 63.33(C-1), 67.98(C-16), 84.80(C-15).

(2-1) Production of tert-butyl (2-iodo-3-methoxyphenyl)-carbamate (16a)

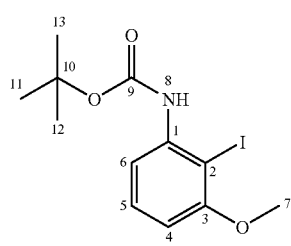

(16a)

To the solution of tert-butyl (3-methoxyphenyl)-carbamate (5 g, 22.4 mmol, 1 eq) in dry diethyl ether (50 mL) was added pentane solution of t-BuLi (35 mL, 49.3 mmol, 2.2 eq) at −20° C., and the mixture was stirred at 3 hours. To this mixed solution was added the solution of iodine (6.83 g, 26.9 mmol, 1.2 eq) in diethylether (60 mL) at −78° C., and after heating the whole solution to room temperature, the solution was stirred for 20 hours. After adding saturated aqueous solution of $Na_2S_{2O3}$ (100 mL), the mixture was extracted three times with diethyl ether (100 mL). The extract was washed with aqueous solution of sodium chloride, dried over magnesium sulfate, and concentrated under reduced pressure. The resulting concentrate was applied to silica gel (eluate: hexane-AcOEt=90-10) to give white solid of the title compound (5.755 g, yield 74%).

MW: ($C_{12}H_{16}INO_3$) 349.17. TLC: (hexane-AcOEt: 8-2) Rf=0.59. m.p.: 69-71° C. $^1$H NMR (300 MHz, $CDCl_3$), δ: 1.53(s, 9H, H-11,12,13), 3.88(s, 3H, H-7), 6.53 (dd, J=8.4 Hz, J=1.3 Hz, 1H, H-6), 7.04(s, 1H, H-8) 7.25(td, J=8.4 Hz, J=0.4 Hz, 1H, H-5), 7.73(dd, J=8.4 Hz, J=1.3 Hz, 1H, H-4). $^{13}$C NMR (75 MHz, $CDCl_3$), δ: −28.3(C-11, 12, 13), 56.5 (C-7), 80.95(C-10), 90.10(C-2), 105.40(C-4), 112.5(C-6), 129.63(C-5), 13.76(C-1), 153.39(C-3), 158.23(C-9).

(2-2) Production of tert-butyl (2-iodo-6-methoxyphenyl)-carbamate (16b)

The title compound (16b) was obtained by a procedure similar to (2-1) (yield 46%).

(2-3) Production of tert-butyl (2-iodo-4-methoxyphenyl)-carbamate (16c)

The title compound (16c) was obtained by a procedure similar to (2-1) (yield 26%).

(3-1) Production of tert-butyl {2-[16-(tert-butyl-dimethylsilanoxy)-hexadecane-1-ynyl]-4-methoxyphenyl}-carbamate (17a, n=14)

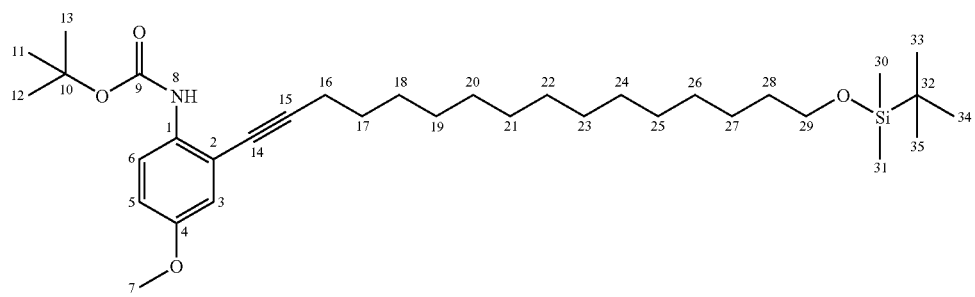

(17a, n = 14)

A mixture of tert-butyl-hexadecane-15-ynyloxy-dimethylsilane (757 mg, 2.15 mmol, 1.5 eq), tert-butyl (2-iodo-4-methoxyphenyl)carbamate (500 mg, 1.43 mmol, 1 eq), [Pd (PPh$_3$)$_2$Cl$_2$] (45 mg, 0.064 mmol, 0.05 eq), CuI (12 mg, 0.064 mmol, 0.05 eq), and Et$_3$N(5 mL) was refluxed for 24 hours. Water (50 mL) and AcOEt (60 mL) were added to the reaction mixture, and the solution was filtered through celite. The filtrate was extracted three times with AcOEt (100 mL). The extract was washed with aqueous solution of sodium chloride, dried over magnesium sulfate, and concentrated under reduced pressure. The resulting concentrate was subjected to silica gel flush chromatography (eluate: hexane-AcOEt=98-2) to obtain pale yellow liquid of the title compound (754 mg, yield 92%).

MW: (C$_{34}$H$_{59}$NO$_4$Si) 573.92. TLC: (hexane-AcOEt: 9-1) Rf=0.49. $^1$H NMR (300 MHz, CDCl$_3$), δ: 0.04(s, 6H, H-30,31), 0.89(s, 9H, H-33,34,35), 1.26-1.70(m, 24H, H-17 to 28), 1.50(s, 9H, H-32,33,34), 2.48(t, J=6.9 Hz, 2H, H-16), 3.59(t, J=6.6 Hz, 2H, H-29), 3.76(s, 3H, H-7), 6.81(m, 2H, H-3, 5), 7.07(s, H-8), 7.96(d, J=8.8 Hz, 1H, H-6). $^{13}$C NMR (75 MHz, CDCl$_3$), δ: −5.28(C-30, 31), 18.35(C-32), 19.55 (C-16), 25.78(C-33, 34, 35), 25.96(C-27), 28.34-29.64(C-17 to C-26), 32.87(C-28), 55.52(C-7), 63.32(C-29), 76.05(C-14), 80.29(C-10), 97.29(C-15), 115.01(C-5), 116.06(C-6), 118.96(C-3), 133.12(C-1), 152.69(C-4), 154.32(C-9).

(3-2)

The following compounds were produced by procedures similar to (3-1). The yield is shown in Table 7.

tert-butyl {2-[18-(tert-butyl-dimethylsilanoxy)-octadecane-1-ynyl]-4-methoxyphenyl}-carbamate (17a, n=16),
tert-butyl {2-[16-(tert-butyl-dimethylsilanoxy)-hexadecane-1-ynyl]-3-methoxyphenyl}-carbamate (17b, n=14),
tert-butyl {2-[18-(tert-butyl-dimethylsilanoxy)-octadecane-1-ynyl]-3-methoxyphenyl}-carbamate (17b, n=16),
tert-butyl {2-[16-(tert-butyl-dimethylsilanoxy)-hexadecane-1-ynyl]-6-methoxyphenyl}-carbamate (17c, n=14)
tert-butyl {2-[18-(tert-butyl-dimethylsilanoxy)-octadecane-1-ynyl]-6-methoxyphenyl}-carbamate (17c, n=16)

TABLE 7

| | | Y = —(CH$_2$)$_n$OH | |
|---|---|---|---|
| | R | n | Yield |
| 17a | 4-MeO | 14 | 92% |
| | | 16 | 90% |
| 17b | 3-MeO | 14 | 75% |
| | | 16 | 61% |
| 17c | 6-MeO | 14 | 57% |
| | | 16 | 37% |

(4-1) Production of 14-(5-methoxy-1H-indol-2-yl)-tetradecane-1-ol (1-2a, n=14)

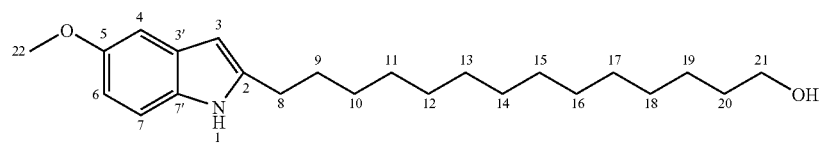

(1-2a, n = 14)

A mixture of 1M THF solution of TBAF (5.1 mL, 5.11 mmol, 15 eq) and tert-butyl {2-[16-(tert-butyl-dimethylsilanoxy)-hexadecynyl]-4-methoxyphenyl}-carbamate (195 mg, 0.34 mmol, 1 eq) was refluxed for 24 hours. After removing THF, the residue was diluted with 50 mL of water, and extracted three times with AcOEt (50 mL). The extract was washed with aqueous solution of sodium chloride, dried over magnesium sulfate, and concentrated. The resulting concentrate was subjected to silica gel flush chromatography (eluate: hexane-AcOEt=70-30) to give white solid of the title compound (79.1 mg, yield 81%).

MW: (C$_{23}$H$_{37}$NO$_2$) 359.55. TLC: (hexane-AcOEt: 7-3) Rf=0.3. m.p.: 68-69° C. $^1$H NMR (300 MHz, CDCl$_3$), δ: 1.26(s br, 20H, H-10 to 19), 1.52-1.72(m, 4H, H-9,20), 2.72(t, J=7.4 Hz, 2H, H-8), 3.64(t, J=6.6 Hz, 2H, H-21), 3.84(s, 3H, H-22), 6.16(s, 1H, H-3), 6.77(dd, J=8.8 Hz, J=2.2 Hz, 1H, H-6), 7.0(d, J=2.2 Hz, 1H, H-4), 7.17(d, J=8.8 Hz, 1H, H-7), 7.78(s, 1H, H-1) $^{13}$C NMR (75 MHz, CDCl$_3$), δ: 25.71(C-19), 28.35(C-8), 29.22-29.58(C-9 to 18), 32.79 (C-20), 55.90(C-22), 63.08(C-21), 99.33(C-3), 101.99(C-6), 110.67(C-7), 110.83(C-4), 129.31(C-3'), 130.90(C-7'), 140.89(C-2), 154.07(C-5). analysis (%): calculated in terms of C$_{23}$H$_{37}$NO$_2$: C=76.83; H=10.37; N=3.9. found: C=76.99; H=10.51; N=3.82.

MS: 359.3 (M$^+$, 63), 173.9 (C$_{11}$H$_{13}$NO, 66), 160.1 (C$_{10}$H$_{11}$NO, 100) UV: (acetonitrile): λ$_{max}$ 219 nm (ε 25575), 294 nm (ε 6951), 306 nm (ε 4292).

(4-2)

The following indole derivatives (1-2) were obtained by procedures similar to (4-1). The yield is shown in Table 8.

16-(5-methoxy-1H-indol-2-yl)-hexadecane-1-ol (1-2a, n=16)

MW: (C$_{25}$H$_{41}$NO$_2$) 387.60 TLC: (hexane-AcOEt: 7-3) Rf=0.29. $^1$H NMR (300 MHz, CDCl$_3$), δ: 1.26(s br, 24H, H-10 to 21), 1.52-1.72(m, 4H, H-9,22), 2.72(t, J=7.4 Hz, 2H, H-8), 3.64(t, J=6.6 Hz, 2H, H-23), 3.84(s, 3H, H-24), 6.16(s, 1H, H-3), 6.76(dd, J=8.8 Hz, J=2.2 Hz, 1H, H-6), 7.01(d, J=2.2 Hz, 1H, H-4), 7.17(d, J=8.8 Hz, 1H, H-7), 7.77(s, 1H, H-1). $^{13}$C NMR (75 MHz, CDCl$_3$), δ: 25.71(C-21), 28.35 (C-8), 29.22-29.58(C-9 to 20), 32.79(C-22), 55.90(C-24), 63.08(C-23), 99.33(C-3), 101.99(C-6), 110.67(C-7), 110.83 (C-4), 129.31(C-3'), 130.90(C-7'), 140.89(C-2), 154.07(C-5). analysis (%): calculated in terms of C$_{25}$H$_{41}$NO$_2$: C=77.47; H=10.66; N=3.61. found: C=77.64; H=10.84; N=3.43.

14-(4-methoxy-1H-indol-2-yl)-tetradecane-1-ol (1-2b, n=14)

MW: (C$_{23}$H$_{37}$NO$_2$) 359.55 TLC: (hexane-AcOEt: 7-3) Rf=0.37. $^1$H NMR (300 MHz, CDCl$_3$), δ: 1.26(s br, 20H, H-10 to 19), 1.52-1.75(m, 4H, H-9,20), 2.73(t, J=7.6 Hz, 2H, H-8), 3.64(t, J=6.9 Hz, 2H, H-21), 3.95(s, 3H, H-22), 6.33(s, 1H, H-3), 6.50(d, J=7.9 Hz, 1H, H-5), 6.93(d, J=7.9 Hz, 1H, H-7), 7.04(t, J=7.9 Hz, 1H, H-6) 7.91(s, 1H, H-1). $^{13}$C NMR (75 MHz, CDCl$_3$), δ: 25.71(C-19), 28.18(C-8), 29.19-29.59

(C-9 to 18), 32.79(C-20), 55.29(C-22), 63.10(C-21), 96.46 (C-3), 99.58(C-7), 103.86(C-5), 119.14(C-3'), 121.59(C-6) 137.10(C-7'), 138.45(C-2), 152.59(C-4). analysis (%): calculated in terms of $C_{23}H_{37}NO_2$: C=76.83; H=10.37; N=3.9. found: C=76.90; H=10.45; N=3.79.

16-(4-methoxy-1H-indole-2-yl)-hexadecane-1-ol
(1-2b, n=16)

MW: ($C_{25}H_{41}NO_2$) 387.60 TLC: (hexane-AcOEt: 7-3) Rf=0.37. $^1$H NMR (300 MHz, CDCl$_3$), δ: 1.25(s br, 24H, H-10 to 21), 1.52-1.73(m, 4H, H-9,22), 2.73(t, J=7.6 Hz, 2H, H-8), 3.64(t, J=6.9 Hz, 2H, H-23), 3.94(s, 3H, H-24), 6.33(s, 1H, H-3), 6.50(d, J=7.9 Hz, 1H, H-5), 6.93(d, J=7.9 Hz, 1H, H-7), 7.03(t, J=7.9 Hz, 1H, H-6), 7.89(s, 1H, H-1). $^{13}$C NMR (75 MHz, CDCl$_3$), δ: 25.72(C-21), 28.18(C-8), 29.19-29.62(C-9 to 20), 32.79(C-22), 55.29(C-24), 63.10(C-23), 96.47(C-3), 99.58(C-7), 103.85(C-5), 119.14(C-3'), 121.59 (C-6), 137.11(C-7'), 138.45(C-2), 152.59(C-4). analysis (%): calculated in terms of $C_{25}H_{41}NO_2$: C=77.47; H=10.66; N=3.61. found: C=77.40; H=10.82; N=3.46.

14-(7-methoxy-1H-indole-2-yl)-tetradecane-1-ol
(1-2c, n=14)

MW: ($C_{23}H_{37}NO_2$) 359.55 TLC: (hexane-AcOEt: 7-3) Rf=0.48. $^1$H NMR (300 MHz, CDCl$_3$), δ: 1.26(s br, 20H, H-10 to 19), 1.52-1.73(m, 4H, H-9,20), 2.74(t, J=7.7 Hz, 2H, H-8), 3.64(t, J=6.6 Hz, 2H, H-21), 3.95(s, 3H, H-22), 6.21(s, 1H, H-3), 6.58(d, J=7.8 Hz, 1H, H-6), 6.98(t, J=7.8 Hz, 1H, H-5), 7.14(d, J=7.8 Hz, 1H, H-4), 8.12(s, 1H, H-1). $^{13}$C NMR (75 MHz, CDCl$_3$), δ: 25.72(C-19), 28.05(C-8), 28.88-29.59(C-9 to 18), 32.79(C-20), 55.21(C-22), 63.09(C-21), 99.75(C-3), 101.07(C-6), 112.63(C-4), 119.80(C-5), 122.58 (C-3'), 130.08(c-7'), 139.60(C-2), 145.50(C-7). analysis (%): calculated in terms of $C_{23}H_{37}NO_2$: C=76.83; H=10.37; N=3.9. found: C=75.51; H=10.30; N=3.40.

16-(7-methoxy-1H-indole-2-yl)-hexadecane-1-ol
(1-2c, n=16)

MW: ($C_{25}H_{41}NO_2$) 387.60 TLC: (hexane-AcOEt: 7-3) Rf=0.49. $^1$H NMR (300 MHz, CDCl$_3$), δ: 1.26(s br, 24H, H-10 to 21), 1.52-1.73(m, 4H, H-9,22), 2.74(t, J=7.7 Hz, 2H, H-8), 3.64(t, J=6.6 Hz, 2H, H-23), 3.95(s, 3H, H-24), 6.20(s, 1H, H-3), 6.58(d, J=7.8 Hz, 1H, H-6), 6.98(t, J=7.8 Hz, 1H, H-5), 7.14(d, J=7.8 Hz, 1H, H-4) 8.13(s, 1H, H-1). $^{13}$C NMR (75 MHz, CDCl$_3$), δ: 25.72(C-21), 28.23(C-8), 29.27-29.61 (C-9 to 20), 32.79(C-22), 55.24(C-24), 63.09(C-23), 99.76 (C-3), 101.04(C-6), 112.62(C-4), 119.80(C-5), 122.59(C-3'), 130.06(C-7'), 139.62(C-2), 145.52(C-7). analysis (%): calculated in terms of $C_{25}H_{41}NO_2$: C=77.47; H=10.66; N=3.61. found: C=77.65; H=10.92; N=3.32.

TABLE 8

| | R | Y = —(CH$_2$)$_n$OH n | Yield |
|---|---|---|---|
| 1-2a | 5-MeO | 14 | 81% |
| | | 16 | 77% |
| 1-2b | 4-MeO | 14 | 84% |
| | | 16 | 76% |
| 1-2c | 7-MeO | 14 | 66% |
| | | 16 | 58% |

Test Example 1

Neural stem cell was produced from ES cell in accordance with the method of Weiss and Reynolds (1996). More specifically, striate body was extirpated from mouse embryo, and the cells were dispersed in a culture medium containing EGF (20 ng/mL). The cells were cultured under the conditions of 5% $CO_2$ and 37° C. for 5 days. The culture was then centrifuged at 400 rpm in Dissociation Medium (manufactured by Sigma) for 5 minutes, and neurospheres which are cluster of the neural stem cells were obtained. The neurospheres were dispersed in the culture medium, and cultivation was conducted under the same conditions to produce secondary neurospheres.

A sterilized cover glass was placed in the well of 24 well plate, treated overnight with polyornithine solution (30 µg/mL), and washed three times with phosphate buffered saline. Neurospheres were inoculated on the cover glass at 20 to 50 cells/cover glass. The test compound that has been adjusted to the concentration of $10^{-6}$M with ethanol was applied to the cover glass, and the cultivation was continued for a period sufficient for differentiation of the neurospheres (typically 24 hours). The indole derivatives obtained in the Examples were used for the test compounds, and the control cells were cultivated without using such test compound.

Sufficiently differentiated neurospheres were fixed with 4% p-formaldehyde, washed with phosphate buffered saline, and after adding Triton-X100, washed again with phosphate buffered saline. Anti-MAP2 (2a+2b) (Sigma) which is a mouse monoclonal antibody used for labeling neurons and Anti-O4 (Boeringher) which is a mouse monoclonal antibody used for labeling oligodendrocytes, and Anti-GFAP (DAKO) which is a rabbit monoclonal antibody used for labeling astrocytes were added, and the cultivation was continued at room temperature for 1 hour or overnight at 4° C. Anti-mouse IgM antibody and fluorescence indicator were added, and cultivation was continued at room temperature for 1 hour. After washing with phosphate buffered saline, the cover glass was placed on a confocal microscope to observe the differentiation of the neurospheres. The results are shown in Table 9.

TABLE 9

| | R | X = —(CH$_2$)$_n$OH n | Y = —(CH$_2$)$_n$OH n | Percentage of neuron in relation to control | Induction of differentiation |
|---|---|---|---|---|---|
| Control | | | | 100 | + |
| 1-1b | 4-MeO | 16 | | 133 | + |
| 1-1a | 5-MeO | 14 | | 143 | ++ |
| | | 16 | | 168 | ++ |
| | | 18 | | 169 | ++ |
| 1-1c | 6-MeO | 16 | | 135 | ++ |
| | | 18 | | 156 | ++ |
| 1-2a | 4-MeO | | 16 | 135 | ++ |
| 1-2b | 5-MeO | | 14 | 147 | ++ |
| | | | 16 | 184 | ++ |
| 1-2c | 7-MeO | | 16 | 128 | + |

The results shown in Table 9 confirm that the indole derivative (1) of the present invention has the action of inducing differentiation of the neurospheres which are clusters of neural stem cells into neurons.

INDUSTRIAL APPLICABILITY

The indole derivative (1) of the present invention has the action of inducing differentiation of neural stem cell specifically into neuron, and this indole derivative is useful as a prophylactic or therapeutic drug for brain dysfunction (e.g. dementia of the Alzheimer type and Parkinson's disease) or neuropathy (e.g. motor paralysis) caused by loss or degeneration of the neuron, and as an agent for promoting differentiation of the stem cell.

The invention claimed is:

1. An indole compound represented by the following formula (1):

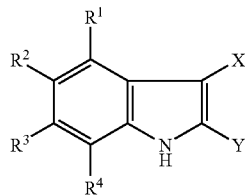

wherein one of $R^1$, $R^2$, $R^3$, and $R^4$ represents an alkoxy group of 1 to 20 carbon atoms, and other groups of the $R^1$, $R^2$, $R^3$, and $R^4$ represent hydrogen or an alkyl group of 1 to 6 carbon atoms; and either one of X and Y represents —$(CH_2)_n$OH wherein n is an integer of 10 to 30, and the other one of the X and Y represents hydrogen atom; or a salt thereof.

2. The indole compound or its salt according to claim 1 wherein one of $R^1$, $R^2$, $R^3$, an $R^4$ is an alkoxy group of 1 to 10 carbon atoms; and other groups of the $R^1$, $R^2$, $R^3$, and $R^4$ are hydrogen; and n is 10 to 20.

3. A pharmaceutical composition comprising the indole compound or its salt of claim 1 and a pharmaceutically acceptable carrier.

4. A process for producing the pharmaceutical composition of claim 3, comprising combining said indole compound and said pharmaceutically acceptable carrier.

5. The indole compound or its salt according to claim 1 wherein $R^1$ represents an alkoxy group; $R^2$, $R^3$, and $R^4$ represent hydrogen; and X represents —$(CH_2)_n$OH.

6. The indole compound or its salt according to claim 1 wherein $R^2$ represents an alkoxy group; $R^1$, $R^3$, and $R^4$ represent hydrogen; and X represents —$(CH_2)_n$OH.

7. The indole compound or its salt according to claim 1 wherein $R^3$, represents an alkoxy group; $R^1$, $R^2$, and $R^4$ represent hydrogen; and X represents —$(CH_2)_n$OH.

8. The indole compound or its salt according to claim 1 wherein $R^4$ represents an alkoxy group; $R^1$, $R^2$, and $R^3$ represent hydrogen; and X represents —$(CH_2)_n$OH.

9. The indole compound or its salt according to claim 1 wherein $R^1$ represents an alkoxy group; $R^2$, $R^3$, and $R^4$ represent hydrogen; and Y represents —$(CH_2)_n$OH.

10. The indole compound or its salt according to claim 1 wherein $R^2$ represents an alkoxy group; $R^1$, $R^3$, and $R^4$ represent hydrogen; and Y represents —$(CH_2)_n$OH.

11. The indole compound or its salt according to claim 1 wherein $R^3$, represents an alkoxy group; $R^1$, $R^2$, and $R^4$ represent hydrogen; and Y represents —$(CH_2)_n$OH.

12. The indole compound or its salt according to claim 1 wherein $R^4$ represents an alkoxy group; $R^1$, $R^2$, and $R^3$ represent hydrogen; and Y represents —$(CH_2)_n$OH.

13. The indole compound or its salt according to claim 1 wherein n is at least 14.

14. An indole compound represented by the following formula (1):

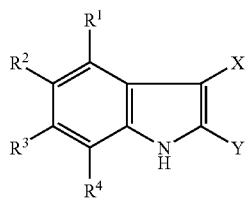

wherein at least one of $R^1$, $R^2$, $R^3$, and $R^4$ represents an alkoxy group of 1 to 20 carbon atoms, and other groups of the $R^1$, $R^2$, $R^3$, and $R^4$ represent hydrogen, an alkyl group of 1 to 6 carbon atoms, acetyl group, or hydroxyl group; and either one of X and Y represents —$(CH_2)_n$OH wherein n is an integer of 10 to 30, and the other one of the X and Y represents hydrogen atom; or a salt thereof.

15. An indole compound represented by the following formula (1):

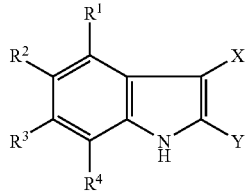

wherein at least one of $R^1$, $R^2$, $R^3$, and $R^4$ represents an alkoxy group of 1 to 20 carbon atoms, and other groups of the $R^1$, $R^2$, $R^3$, and $R^4$ represent hydrogen or an alkyl group of 1 to 6 carbon atoms; and either one of X and Y represents —$(CH_2)_n$OH wherein n is an integer of 10 to 30, and the other one of the X and Y represents hydrogen atom; or a salt thereof.

* * * * *